(12) United States Patent
Fischer et al.

(10) Patent No.: US 8,846,696 B2
(45) Date of Patent: *Sep. 30, 2014

(54) PURINE DERIVATIVES

(75) Inventors: Peter Martin Fischer, Beeston (GB); Michael Jarman, London (GB); Edward McDonald, Reigate (GB); Bernard Nutley, Sutton (GB); Florence Raynaud, London (GB); Stuart Wilson, Sutton (GB); Paul Workman, Abinger Common (GB)

(73) Assignees: Cyclacel Limited, London (GB); Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/489,663

(22) Filed: Jun. 23, 2009

(65) Prior Publication Data

US 2009/0325983 A1 Dec. 31, 2009

Related U.S. Application Data

(63) Continuation of application No. 11/033,692, filed on Jan. 11, 2005, now Pat. No. 7,582,642, which is a continuation of application No. PCT/GB03/03554, filed on Aug. 13, 2003.

(30) Foreign Application Priority Data

Aug. 15, 2002 (GB) .................................. 0219054.4

(51) Int. Cl.
*A61K 31/52* (2006.01)
*C07D 473/16* (2006.01)

(52) U.S. Cl.
CPC ............. *C07D 473/16* (2013.01); *A61K 31/52* (2013.01)
USPC ..................... 514/263.22; 544/277

(58) Field of Classification Search
USPC ........................................................ 544/277
See application file for complete search history.

(56) References Cited

U.S. PATENT DOCUMENTS

| | | | |
|---|---|---|---|
| 6,627,633 | B2 | 9/2003 | Trova |
| 7,544,689 | B2 * | 6/2009 | Fischer et al. ............ 514/263.22 |
| 7,582,642 | B2 * | 9/2009 | Fischer et al. ............ 514/263.22 |
| 7,612,079 | B2 * | 11/2009 | Fischer et al. ............ 514/263.22 |
| 2002/0049218 | A1 | 4/2002 | Meijer et al. |
| 2002/0091263 | A1 | 7/2002 | Trova |
| 2003/0087906 | A1 | 5/2003 | Trova |
| 2003/0092909 | A1 | 5/2003 | Trova |
| 2003/0229105 | A1 | 12/2003 | Kashanchi |
| 2005/0009846 | A1 | 1/2005 | Fischer et al. |
| 2005/0256142 | A1 | 11/2005 | Fischer et al. |
| 2006/0183760 | A1 | 8/2006 | Fischer et al. |
| 2010/0093769 | A1 * | 4/2010 | Sheldrake et al. ....... 514/263.22 |

FOREIGN PATENT DOCUMENTS

| | | |
|---|---|---|
| WO | WO-97/16452 A1 | 5/1997 |
| WO | WO-97/20842 A1 | 6/1997 |
| WO | WO-98/05335 A1 | 2/1998 |
| WO | WO-98/16528 A1 | 4/1998 |
| WO | WO-99/07705 A1 | 2/1999 |
| WO | WO-99/34018 A1 | 7/1999 |
| WO | WO-99/43676 A2 | 9/1999 |

(Continued)

OTHER PUBLICATIONS

"50% of what? How exactly are IC50 and EC50 defined?" <http://www.graphpad.com/support/faqid/1356/> downloaded from the internet Nov. 2, 2012.*

(Continued)

*Primary Examiner* — Golam M M Shameem
*Assistant Examiner* — Laura Daniel
(74) *Attorney, Agent, or Firm* — Nelson Mullins Riley & Scarborough LLP; Jane E. Remillard, Esq.; Cynthia L. Kanik

(57) ABSTRACT

The present invention relates to compounds of formula 1

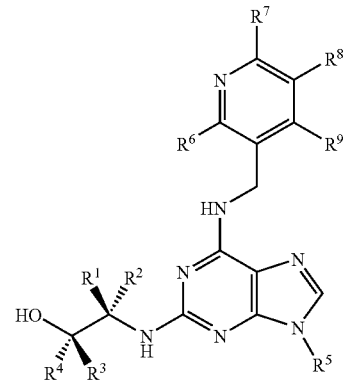

or pharmaceutically acceptable salts thereof, wherein one of $R^1$ and $R^2$ is methyl, ethyl or isopropyl, and the other is H;

$R^3$ and $R^4$ are each independently H, branched or unbranched $C_1$-$C_6$ alkyl, or aryl, and wherein at least one of $R^3$ and $R^4$ is other than H;

$R^5$ is a branched or unbranched $C_1$-$C_5$ alkyl group or a $C_1$-$C_6$ cycloalkyl group, each of which may be optionally substituted with one or more OH groups;

$R^6$, $R^7$, $R^8$ and $R^9$ are each independently H, halogen, $NO_2$, OH, OMe, CN, $NH_2$, COOH, $CONH_2$, or $SO_2NH_2$.

A further aspect of the invention relates to pharmaceutical compositions comprising compounds of formula 1, and the use of said compounds in treating proliferative disorders, viral disorders, stroke, alopecia, CNS disorders, neurodegenerative disorders, or diabetes.

6 Claims, No Drawings

(56) References Cited

FOREIGN PATENT DOCUMENTS

| WO | WO-00/44750 A1 | 8/2000 |
| WO | WO-00/55161 A1 | 9/2000 |
| WO | WO-03/002565 A1 | 1/2003 |

OTHER PUBLICATIONS

Thompson, Thomas N. Medicinal Research Reviews, vol. 21, No. 5, 412-449, 2001.*
Chang, Young-Tae et al., "Synthesis and application of functionally diverse 2, 6, 9-trisubstituted purine libraries as CDK inhibitors," *Chemistry & Biology*, vol. 6(6):361-375 (1999).
De Azevedo, Walter Filgueira et al., "Inhibition of cyclin-dependent kinases by purine analogues: Crystal structure of human cdk2 complexed with roscovitine," *Eur. J. Biochem*, vol. 243:518-526 (1997).
Ducrot, Pierre et al., "3D-QSAR CoMFA on Cyclin-Dependent Kinase Inhibitors," *J. Med. Chem.*, vol. 43:4098-4108 (2000).
Giocanti, Nicole et al., "In Vitro Evaluation of a Novel 2, 6, 9-Trisubstituted Purine Acting as a Cyclin-Dependent Kinase Inhibitor," *Annals of the New York Academy of Sciences*, vol. 886:180-182.
Gray, Nathanael et al., "ATP-site Directed Inhibitors of Cyclin-dependent Kinases," *Current Medicinal Chemistry*, vol. 6:859-875 (1999).
Gray, Nathanael S. et al., "Exploiting Chemical Libraries, Structure, and Genomics in the Search for inase Inhibitors," *Science*, vol. 281:533-538 (1998).
Imbach, Patricia et al., "2, 6, 9-Trisubstituted Purines: Optimization Towards Highly Potent and Selective CDK1 Inhibitors," *Bioorganic & Medicinal Chemistry Letters*, vol. 9:91-96 (1999).
Legraverend, Michel et al., "Synthesis and in Vitro Evaluation of Novel 2, 6, 9-Trisubstituted Purines Acting as Cyclin-dependent Kinase Inhibitors," *Bioorganic & Medicinal Chemistry*, vol. 7:1281-1293 (1999).
Legraverend, Michel et al., "Synthesis of C2 Alkynyated Purines, a New Family of Potent Inhibitors of Cyclin-Dependent Kinases," *Boorganic & Medicinal Chemistry Letters*, vol. 8:793-798 (1998).
Oh, Chang-Hyun et al., "Synthesis and Biological Activities of C-2, N-9 Substituted 6-Benzylaminopurine Derivatives as Cyclin-Dependent Kinase Inhibitor," *Arch. Pharm. Pharm.Med. Chem.*, vol. 332:187-190 (1999).
Schow, Steven R. et al., "Synthesis and Activity of 2, 6, 9-Trisubstituted Purines," *Bioorganic & Medicinal Chemistry Letters*, vol. 7(21):2697-2702 (1997).
Vesely, Jaroslav et al., "Inhibition of cyclin-dependent kinases by purine analogues," *Eur. J. Biochem*, vol. 224:771-786 (1994).
Di et al., "Optimization of a higher throughput microsomal stability screening assay for profiling drug discovery candidates," *J. Biomol. Screen.* 8(4):453-462, 2003.
Humphreys et al., "Application of structure-metabolism relationships in the identification of a selective endothelin a antagonist, BMS-193884, with favourable pharmacokinetic properties," *Xenobiotica* 33(11):1109-1123, 2003.
Korfmacher et al., "Development of an automated mass spectrometry system for the quantitative analysis of liver microsomal incubation samples: a tool for rapid screening of new compounds for metabolic stability," *Rapid Commun. Mass Spectrom.* 13(10):901-907, 1999.
Linget et al., "Automation of metabolic stability studies in microsomes, cytosol and plasma using a 215 Gilson liquid handler," *J. Pharm. Biomed. Anal.* 19(6):893-901, 1999.
Riley et al., "A unified model for predicting human hepatic, metabolic clearance from in vitro intrisic clearance data in hepatocytes and microsomes," *Drug Metabolism and Disposition* 33:1304, 2005.
Tong et al., "Determination of an arylether antiarrythmic and its N-dealkyl metabolite in rat plasma and hepatic microsomal incubates using liquid chromatography-tandem mass spectrometry," *J. Chromatogr. B. Biomed. Sci. Appl.* 759(2):259-266, 2001.
Wilson et al., "Design, Synthesis and biological evaluation of 6-pyridylmethylaminopurines as CDK inhibitors," *Bioorg. Med. Chem.* 19:6949-6965, 2011.

* cited by examiner

PURINE DERIVATIVES

RELATED APPLICATIONS

This application is a continuation of U.S. application Ser. No. 11/033,692, filed Jan. 11, 2005, which is a continuation of PCT/GB2003/003554, filed Aug. 13, 2003, which claims priority to GB 0219054.4, filed Aug. 15, 2002. The entire contents of these applications are hereby incorporated herein by reference.

FIELD OF INVENTION

The present invention relates to new 2,6,9-substituted purine derivatives and their biological applications. In particular, the invention relates to purine derivatives having antiproliferative properties which are useful in the treatment of proliferative disorders such as cancer, leukemia, psoriasis and the like.

BACKGROUND

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1), cyclin D1-D3 (CDK2, CDK4, CDK5, CDK6), cyclin E (CDK2). Each of these complexes is involved in a particular phase of the cell cycle. Not all members of the CDK family are involved exclusively in cell cycle control, however. Thus CDKs 7, 8, and 9 are implicated in the regulation of transcription, and CDK5 plays a role in neuronal and secretory cell function.

The activity of CDKs is regulated post-translationally, by transitory associations with other proteins, and by alterations of their intracellular localisation. Tumour development is closely associated with genetic alteration and deregulation of CDKs and their regulators, suggesting that inhibitors of CDKs may be useful anti-cancer therapeutics. Indeed, early results suggest that transformed and normal cells differ in their requirement for e.g. cyclin A/CDK2 and that it may be possible to develop novel antineoplastic agents devoid of the general host toxicity observed with conventional cytotoxic and cytostatic drugs. While inhibition of cell cycle-related CDKs is clearly relevant in e.g. oncology applications, this may not be the case for the inhibition of RNA polymerase-regulating CDKs. On the other hand, inhibition of CDK9/cyclin T function was recently linked to prevention of HIV replication and the discovery of new CDK biology thus continues to open up new therapeutic indications for CDK inhibitors (Sausville, E. A. Trends Molec. Med. 2002, 8, S32-S37).

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

WO 98/05335 (CV Therapeutics Inc) discloses 2,6,9-trisubstituted purine derivatives that are selective inhibitors of cell cycle kinases. Such compounds are useful in the treatment of autoimmune disorders, e.g. rheumatoid arthritis, lupus, type I diabetes, multiple sclerosis; treating cancer, cardiovascular disease, such as restenosis, host v graft disease, gout, polycystic kidney disease and other proliferative diseases whose pathogenesis involves abnormal cell proliferation.

WO 99/07705 (The Regents of the University of California) discloses purine analogues that inhibit inter alia protein kinases, G-proteins and polymerases. More specifically, the invention relates to methods of using such purine analogues to treat cellular proliferative disorders and neurodegenerative diseases.

WO 97/20842 (CNRS) also discloses purine derivatives displaying antiproliferative properties which are useful in treating cancer, psoriasis, and neurodegenerative disorders.

The present invention seeks to provide new 2,6,9-substituted purine derivatives, particularly those having antiproliferative properties.

STATEMENT OF INVENTION

A first aspect of the invention relates to a compound of formula I

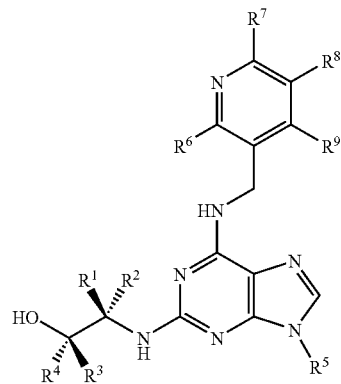

or a pharmaceutically acceptable salt thereof, wherein
one of $R^1$ and $R^2$ is methyl, ethyl or isopropyl, and the other is H;
$R^3$ and $R^4$ are each independently H, branched or unbranched $C_1$-$C_6$ alkyl, or aryl, and wherein at least one of $R^3$ and $R^4$ is other than H;
$R^5$ is a branched or unbranched $C_1$-$C_5$ alkyl group or a $C_1$-$C_6$ cycloalkyl group, each of which may be optionally substituted with one or more OH groups;
$R^6$, $R^7$, $R^8$ and $R^9$ are each independently H, halogen, $NO_2$, OH, OMe, CN, $NH_2$, COOH, $CONH_2$, or $SO_2NH_2$.

A second aspect of the invention relates to a pharmaceutical composition comprising a compound of formula 1 and a pharmaceutically acceptable carrier, diluent or excipient.

A third aspect of the invention relates to the use of a compound of formula 1 in the preparation of a medicament for treating one or more of the following disorders:
 a proliferative disorder;
 a viral disorder;
 a stroke;
 alopecia;
 a CNS disorder;
 a neurodegenerative disorder; and
 diabetes.

A fourth aspect of the invention relates to the use of a compound of formula 1 as an anti-mitotic agent.

A fifth aspect of the invention relates to the use of a compound of formula 1 for inhibiting a protein kinase.

A sixth aspect of the invention relates to a method of treating a proliferative disease, said method comprising administering to a mammal a therapeutically effective amount of a compound of formula 1.

A seventh aspect of the invention relates to the use of a compound of the invention in an assay for identifying further candidate compounds that influence the activity of one or more CDK enzymes.

DETAILED DESCRIPTION

As mentioned above, a first aspect of the invention relates to a compound of formula 1 as defined hereinbefore.

It is known in the art that the main in vivo metabolic deactivation pathway of the experimental anti-proliferative CDK-inhibitory agent roscovitine (refer PCT Intl. Patent Appl. Publ. WO 97/20842; Wang, S., McClue, S. J., Ferguson, J. R., Hull, J. D., Stokes, S., Parsons, S., Westwood, R., and Fischer, P. M. Tetrahedron: Asymmetry 2001, 12, 2891-2894) comprises oxidation of the carbinol group to a carboxyl group and subsequent excretion of this metabolite [Nutley, B. P., Raynaud, F. I., Wilson, S. C., Fischer, P., McClue, S., Goddard, P. M., Jarman, M., Lane, D., and Workman, P. Clin. Cancer Res. 2000, 6 Suppl. (Proc. 11$^{th}$ AACR-NCI-EORTC Intl. Conf. #318)]. Authentic synthetic material identical with this metabolite, shows reduced biological activity in vitro. Thus, roscovitine and the carboxyl derivative inhibit CDK2/cyclin E activity with IC$_{50}$ values of 0.08 and 0.24 μM, respectively. Similarly, the average anti-proliferative IC$_{50}$ values in a representative panel of human transformed tumour cell lines for roscovitine and the carboxyl derivative were ca. 10 and >50 μM, respectively.

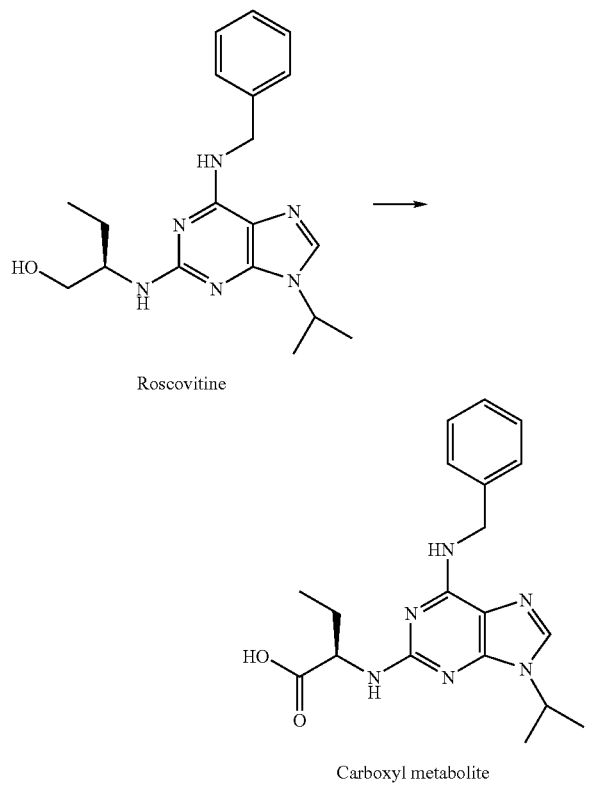 [SMILES: CC[C@H](CO)Nc1nc(NCc2ccccc2)c2ncn(C(C)C)c2n1 ; CC[C@@H](Nc1nc(NCc2ccccc2)c2ncn(C(C)C)c2n1)C(=O)O]

Roscovitine

Carboxyl metabolite

Thus, in one preferred embodiment, the invention seeks to provide new purine derivatives which exhibit improved resistance to metabolic deactivation.

In one preferred embodiment of the invention, one of $R^1$ and $R^2$ is ethyl or isopropyl, and the other is H.

In another preferred embodiment of the invention, $R^5$ is isopropyl or cyclopentyl.

In one preferred embodiment, $R^6$, $R^7$, $R^8$ and $R^9$ are all H.

In one preferred embodiment, $R^1$ or $R^2$ is ethyl and the other is H.

In one preferred embodiment, $R^3$ and $R^4$ are each independently H, methyl, ethyl, propyl, butyl or phenyl.

Thus, in one preferred embodiment, $R^3$ and $R^4$ are each independently H, methyl, ethyl, n-propyl, isopropyl, n-butyl, s-butyl, t-butyl or phenyl.

In a more preferred embodiment, $R^3$ and $R^4$ are each independently H, methyl, ethyl, propyl or butyl.

Thus, in one preferred embodiment, $R^3$ and $R^4$ are each independently H, methyl, ethyl, n-propyl, isopropyl, n-butyl, s-butyl or t-butyl.

In an even more preferred embodiment, $R^3$ and $R^4$ are each independently H, methyl, ethyl, isopropyl or t-butyl.

In one especially preferred embodiment, said compound of formula 1 is selected from the following:
(2S3R)-3-{9-Isopropyl-6-[(pyridin-3-ylmethyl)-amino]-9H-purin-2-ylamino}-pentan-2-ol;
(2R3S)-3-{9-Isopropyl-6-[(pyridin-3-ylmethyl)-amino]-9H-purin-2-ylamino}-pentan-2-ol;
(3RS,4R)-4-{9-Isopropyl-6-[(pyridin-3-ylmethyl)-amino]-9H-purin-2-ylamino}-hexan-3-ol;
(3RS,4S)-4-{9-Isopropyl-6-[(pyridin-3-ylmethyl)-amino]-9H-purin-2-ylamino}-hexan-3-ol;
(3RS,4R)-4-{9-Isopropyl-6-[(pyridin-3-ylmethyl)-amino]-9H-purin-2-ylamino}-2-methyl-hexan-3-ol;
(3RS,4S)-4-{9-Isopropyl-6-[(pyridin-3-ylmethyl)-amino]-9H-purin-2-ylamino}-2-methyl-hexan-3-ol;
(3RS,4R)-4-{9-Isopropyl-6-[(pyridin-3-ylmethyl)-amino]-9H-purin-2-ylamino}-2,2-dimethyl-hexan-3-ol;
(3RS,4S)-4-{9-Isopropyl-6-[(pyridin-3-ylmethyl)-amino]-9H-purin-2-ylamino}-2,2-dimethyl-hexan-3-ol;
(3R)-3-{9-Isopropyl-6-[(pyridin-3-ylmethyl)-amino]-9H-purin-2-ylamino}-2-methyl-pentan-2-ol;
(3S)-3-{9-Isopropyl-6-[(pyridin-3-ylmethyl)-amino]-9H-purin-2-ylamino}-2-methyl-pentan-2-ol;
(3S)-3-{9-Isopropyl-6-[(pyridin-3-ylmethyl)-amino]-9H-purin-2-ylamino}-2-methyl-pentan-2-ol; and
(3R)-3-{9-Isopropyl-6-[(pyridin-3-ylmethyl)-amino]-9H-purin-2-ylamino}-2-methyl-pentan-2-ol.

Even more preferably, said compound of formula 1 is selected from the following:
(2S3R)-3-{9-Isopropyl-6-[(pyridin-3-ylmethyl)-amino]-9H-purin-2-ylamino}-pentan-2-ol;
(2R3S)-3-{9-Isopropyl-6-[(pyridin-3-ylmethyl)-amino]-9H-purin-2-ylamino}-pentan-2-ol;
(3RS,4R)-4-{9-Isopropyl-6-[(pyridin-3-ylmethyl)-amino]-9H-purin-2-ylamino}-hexan-3-ol;
(3RS,4S)-4-{9-Isopropyl-6-[(pyridin-3-ylmethyl)-amino]-9H-purin-2-ylamino}-hexan-3-ol;
(3RS,4S)-4-{9-Isopropyl-6-[(pyridin-3-ylmethyl)-amino]-9H-purin-2-ylamino}-2,2-dimethyl-hexan-3-ol;
(3R)-3-{9-Isopropyl-6-[(pyridin-3-ylmethyl)-amino]-9H-purin-2-ylamino}-2-methyl-pentan-2-ol; and
(3S)-3-{9-Isopropyl-6-[(pyridin-3-ylmethyl)-amino]-9H-purin-3-ylamino}-2-methyl-pentan-2-ol.

More preferably still, said compound of formula 1 is selected from the following:
(3R)-3-{9-isopropyl-6-[(pyridin-3-ylmethyl)-amino]-9H-purin-2-ylamino}-2-methyl-pentan-2-ol;
(3S)-3-{9-isopropyl-6-[(pyridin-3-ylmethyl)-amino]-9H-purin-2-ylamino}-2-methyl-pentan-2-ol;

(2S3R)-3-{9-isopropyl-6-[(pyridin-3-ylmethyl)-amino]-9H-purin-2-ylamino}-pentan-2-ol;
(2R3S)-3-{9-isopropyl-6-[(pyridin-3-ylmethyl)-amino]-9H-purin-2-ylamino}-pentan-2-ol; and
any optical isomer of 3-{9-isopropyl-6-[(pyridin-3-ylmethyl)-amino]-9H-purin-2-ylamino}-pentan-2-ol.

Pharmaceutical Compositions

A second aspect of the invention relates to a pharmaceutical composition comprising a compound of formula 1 admixed with a pharmaceutically acceptable diluent, excipient or carrier, or a mixture thereof. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the present invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of formula 1. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes compounds of the present invention in prodrug form. Such prodrugs are generally compounds of formula 1 wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient for the treatment of malignancy.

Therapeutic Use

The compounds of the present invention have been found to possess anti-proliferative activity and are therefore believed to be of use in the treatment of proliferative disorders, such as cancers, leukaemias or other disorders associated with uncontrolled cellular proliferation such as psoriasis and restenosis.

As defined herein, an anti-proliferative effect within the scope of the present invention may be demonstrated by the ability to inhibit cell proliferation in an in vitro whole cell assay, for example using any of the cell lines A549, HeLa, HT-29, MCF7, Saos-2, CCRF-CEM, HL-60 and K-562, or by showing kinase inhibition in an appropriate assay. These assays, including methods for their performance, are described in more detail in the accompanying Examples. Using such assays it may be determined whether a compound is anti-proliferative in the context of the present invention.

One preferred embodiment of the present invention therefore relates to the use of one or more compounds of the invention in the preparation of a medicament for treating a proliferative disorder.

As used herein the phrase "preparation of a medicament" includes the use of a compound of the invention directly as the medicament in addition to its use in a screening programme for further therapeutic agents or in any stage of the manufacture of such a medicament.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required. Preferably, the proliferative disorder is a cancer or leukaemia.

In another preferred embodiment, the proliferative disorder is psoriasis.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

A further aspect of the invention relates to a method of treating a proliferative disease, said method comprising administering to a mammal a therapeutically effective amount of a compound of formula 1.

In a preferred embodiment of this aspect, the proliferative disorder is cancer or leukaemia.

In an even more preferred embodiment of this aspect, the compound is administered in an amount sufficient to inhibit at least one CDK enzyme.

Preferably, the compound of the invention is administered in an amount sufficient to inhibit at least one of CDK1, CDK2, CDK3, CDK4, CDK6, CDK7, CDK8 and/or CDK9.

More preferably, the compound of the invention is administered in an amount sufficient to inhibit at least one of CDK2 and/or CDK4.

Even more preferably, the CDK enzyme is CDK2.

In one preferred embodiment of this aspect, the compound is administered orally.

Another aspect of the invention relates to the use of a compound of formula 1 as an anti-mitotic agent.

Yet another aspect of the invention relates to the use of a compound of formula 1 for treating a neurodegenerative disorder.

Preferably, the neurodegenerative disorder is neuronal apoptosis.

Another aspect of the invention relates to the use of a compound of formula 1 as an antiviral agent.

Thus, another aspect of the invention relates to the use of a compound of the invention in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

In a more preferred embodiment of the invention, the compound of the invention is administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. J. Virol. 2001; 75: 7266-7279].

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of the invention in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Another aspect of the invention relates to the use of compounds of the invention, or pharmaceutically accetable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes [Chen, Y. H.; Hansen, L.; Chen, M. X.; Bjorbaek, C.; Vestergaard, H.; Hansen, T.; Cohen, P. T.; Pedersen, O. *Diabetes*, 1994, 43, 1234]. Furthermore, it has been demonstrated that GSK3 is over-expressed in muscle cells of type II diabetics and that an inverse correlation exists between skeletal muscle GSK3 activity and insulin action [Nikoulina, S. E.; Ciaraldi, T. P.; Mudaliar, S.; Mohideen, P.; Carter, L.; Henry, R. R. *Diabetes*, 2000, 49, 263].

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of the invention, or pharmaceutically acceptable salts thereof, in the preparation of a medicament for treating a CNS disorders, for example neurodegenerative disorders.

Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process [Goedert, M. *Curr. Opin. Gen. Dev.,* 2001, 11, 343].

Another aspect of the invention relates to the use of compounds of the invention, or pharmaceutically acceptable salts thereof, in the preparation of a medicament for treating bipolar disorder.

Yet another aspect of the invention relates to the use of compounds of the invention, or pharmaceutically acceptable salts thereof, in the preparation of a medicament for treating a stroke.

Reducing neuronal apoptosis is an important therapeutic goal in the context of head trauma, stroke, epilepsy, and motor neuron disease [Mattson, M. P. Nat. Rev. Mol. Cell. Biol., 2000, 1, 120]. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of the invention, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential [Zhu, A. J.; Watt, F. M. Development, 1999, 126, 2285]. This population of stem cells expresses a higher level of non-cadherin-associated β-catenin [DasGupta, R.; Fuchs, E. Development, 1999, 126, 4557], which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia. A further aspect of the invention relates to a method of treating a GSK3-dependent disorder, said method comprising administering to a subject in need thereof, a compound according to the invention, or a pharmaceutically acceptable salt thereof, as defined above in an amount sufficient to inhibit GSK3.

Preferably, the compound of the invention, or pharmaceutically acceptable salt thereof, is administered in an amount sufficient to inhibit GSK3β.

In one embodiment of the invention, the compound of the invention is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities [Sunkel et al., *J. Cell Sci.*, 1988, 89, 25] and polo was found to encode a mitotic kinase [Llamazares et al., *Genes Dev.*, 1991, 5, 2153]. In humans, there exist three closely related PLKs [Glover et al., *Genes Dev.*, 1998, 12, 3777]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [Lee et al., *Proc. Natl. Acad. Sci. USA*, 1998, 95, 9301; Leung et al., *Nat. Struct. Biol.*, 2002, 9, 719], mediation of interactions with other proteins [Kauselmann et al., *EMBO J.*, 1999, 18, 5528], or may constitute part of an autoregulatory domain [Nigg, *Curr. Opin. Cell Biol.*, 1998, 10, 776]. Furthermore, the polo box-dependent PLK1 activity is required for proper metaphase/anaphase transition and cytokinesis [Yuan et al., *Cancer Res.*, 2002, 62, 4186; Seong et al., J. Biol. Chem., 2002, 277, 32282].

Studies have shown that human PLKs regulate some fundamental aspects of mitosis [Lane et al., *J. Cell. Biol.*, 1996, 135, 1701; Cogswell et al., *Cell Growth Differ.*, 2000, 11, 615]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [Liu et al., *Proc. Natl. Acad. Sci. USA*, 2002, 99, 8672].

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis [Toyoshima-Morimoto et al., *Nature*, 2001, 410, 215; Roshak et al., *Cell. Signalling*, 2000, 12, 405], DNA-damage checkpoint activation [Smits et al., *Nat. Cell Biol.*, 2000, 2, 672; van Vugt et al., *J. Biol. Chem.*, 2001, 276, 41656], regulation of the anaphase promoting complex [Sumara et al., *Mol. Cell*, 2002, 9, 515; Golan et al., *J. Biol. Chem.*, 2002, 277, 15552; Kotani et al., *Mol. Cell*, 1998, 1, 371], phosphorylation of the proteasome [Feng et al., *Cell Growth Differ.*, 2001, 12, 29], and centrosome duplication and maturation [Dai et al., *Oncogene*, 2002, 21, 6195].

Specifically, initiation of mitosis requires activation of M-phase promoting factor (MPF), the complex between the cyclin dependent kinase CDK1 and B-type cyclins [Nurse, *Nature*, 1990, 344, 503]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [Nigg, *Nat. Rev. Mol. Cell Biol.*, 2001, 2, 21]. In interphase, cyclin B localizes to the cytoplasm [Hagting et al., *EMBO J.*, 1998, 17, 4127], it then becomes phosphorylated during prophase and this event causes nuclear translocation [Hagting et al., *Curr. Biol.*, 1999, 9, 680; Yang et al., *J. Biol. Chem.*, 2001, 276, 3604]. The nuclear accumulation of active MPF during prophase is thought to be important for initiating M-phase events [Takizawa et al., *Curr. Opin. Cell Biol.*, 2000, 12, 658]. However, nuclear MPF is kept inactive by WEE1 unless counteracted by CDC25C. The phosphatase CDC25C itself, localized to the cytoplasm during interphase, accumulates in the nucleus in prophase [Seki et al., *Mol. Biol. Cell*, 1992, 3, 1373; Heald et al., *Cell*, 1993, 74, 463; Dalal et al., *Mol. Cell. Biol.*, 1999, 19, 4465]. The nuclear entry of both cyclin B [Toyoshima-Morimoto et al., *Nature*, 2001, 410, 215] and CDC25C [Toyoshima-Morimoto et al., *EMBO Rep.*, 2002, 3, 341] are promoted through phosphorylation by PLK1 [Roshak et al., *Cell. Signalling*, 2000, 12, 405]. This kinase is an important regulator of M-phase initiation.

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [Wang et al., *Mol. Cell. Biol.*, 2002, 22, 3450]. PLK2 is the least well understood homologue of the three PLKs. Both PLK2 and PLK3 may have additional important post-mitotic functions [Kauselmann et al., *EMBO J.*, 1999, 18, 5528].

Another aspect of the invention relates to the use of a compound of formula 1 for inhibiting a protein kinase.

In a preferred embodiment of this aspect, the protein kinase is a cyclin dependent kinase. Preferably, the protein kinase is CDK1, CDK2, CDK3, CDK4, CDK6, CDK7, CDK8 or CDK9, more preferably CDK2.

A further aspect of the invention relates to a method of inhibiting a protein kinase, said method comprising contacting said protein kinase with a compound of formula 1.

In a preferred embodiment of this aspect, the protein kinase is a cyclin dependent kinase, even more preferably CDK2.

Assays

Another aspect of the invention relates to the use of a compound as defined hereinabove in an assay for identifying further candidate compounds that influence the activity of one or more CDK enzymes.

Preferably, the assay is capable of identifying candidate compounds that are capable of inhibiting one or more CDK enzymes.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of formula 1 with a CDK enzyme in the presence of a known substrate of said CDK enzyme and detecting any change in the interaction between said CDK enzyme and said known substrate.

A sixth aspect of the invention provides a method of detecting the binding of a ligand to a CDK enzyme, said method comprising the steps of:
(i) contacting a ligand with a CDK enzyme in the presence of a known substrate of said CDK enzyme;
(ii) detecting any change in the interaction between said CDK enzyme and said known substrate;
and wherein said ligand is a compound of formula 1.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders.

The above methods may be used to screen for a ligand useful as an inhibitor of one or more CDK enzymes.

Process

A further aspect of the invention relates to a process for preparing a compound of formula I as defined hereinabove, said process comprising reacting a compound of formula V with a compound of formula VI

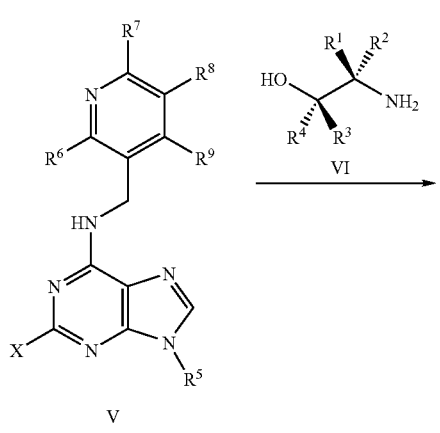

-continued

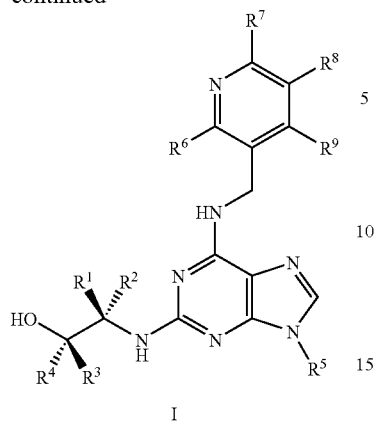

wherein $R^{1-9}$ are as defined in claim 1 and X is Cl or F.

Preferably, said compound of formula V is prepared by the following steps:

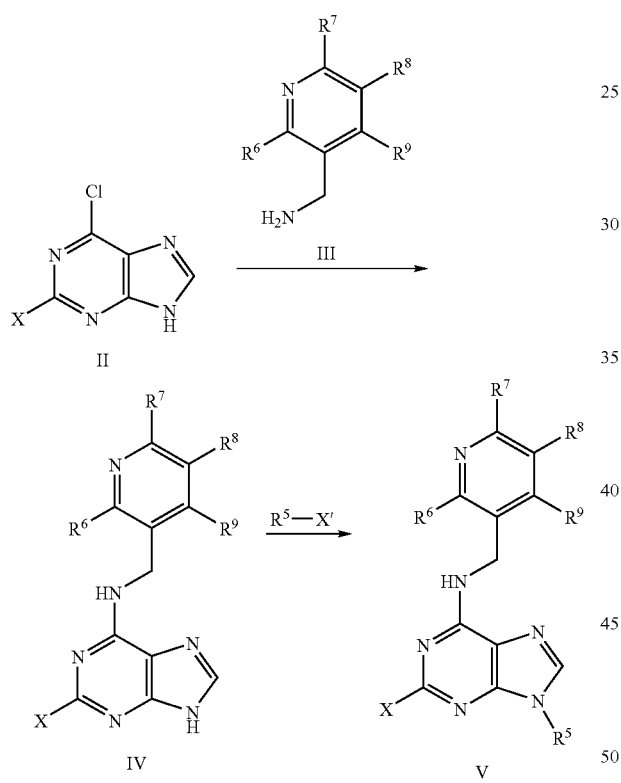

(i) reacting a compound of formula II with a compound of formula III to form a compound of formula IV;
(ii) alkylating said compound of formula IV with an alkyl halide, $R^5$—X', to form a compound of formula V.

Preferably, said compound of formula VI is prepared by the following steps:

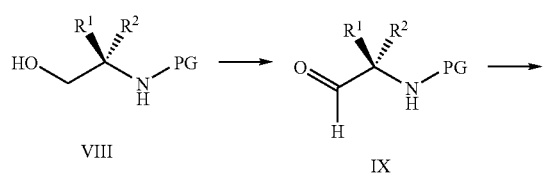

-continued

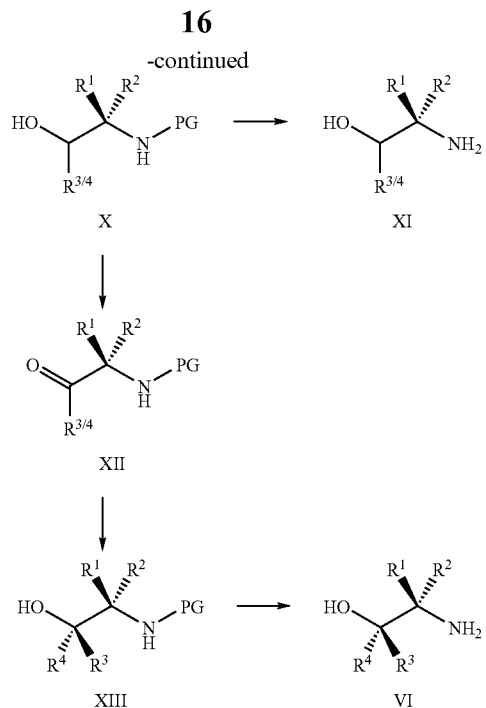

(i) oxidising a compound of formula VIII, wherein PG is a protecting group, to form a compound of formula IX;
(ii) alkylating said compound of formula IX to form a compound of formula X;
(iii) removing protecting group PG from said compound of formula X to form a compound of formula IX, which is equivalent to formula VI (where one of $R^3$ or $R^4$ is H).

Alternatively, said compound of formula VI is prepared by the following steps:

(i) oxidising a compound of formula VIII, wherein PG is a protecting group, to form a compound of formula IX;
(ii) alkylating said compound of formula IX to form a compound of formula X;
(iii) oxidising said compound of formula X to form a compound of formula XI;
(iv) alkylating said compound of formula XI to form a compound of formula XII;
(v) removing protecting group PG from said compound of formula XIII to form a compound of formula VI.

More preferably, the oxidation in steps (i) and (iii) of the above processes are achieved by means of a Swern oxidation.

Preferably, the alkylation reaction of steps (ii) and (iv) of the above processes are achieved by treating the compound with an alkyllithium reagent in the presence of a copper bromide/dimethyl sulfide complex catalyst.

In alternative preferred embodiment, $R^3=R^4$ and said compound of formula VI is prepared by a process which comprises the steps of:

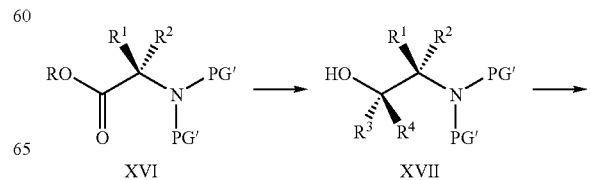

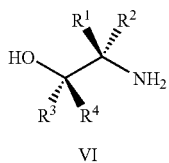

(i) converting a compound of formula XVI, where PG' is a protecting group and R is an alkyl group, to a compound of formula XVII;
(ii) removing protecting groups PG' from said compound of formula XVII to form a compound of formula VI.

Preferably, said compound of formula XVI is converted to a compound of formula XVII via a double Grignard reaction.

More preferably, in respect of this embodiment, said compound of formula VI is is prepared by the following steps:

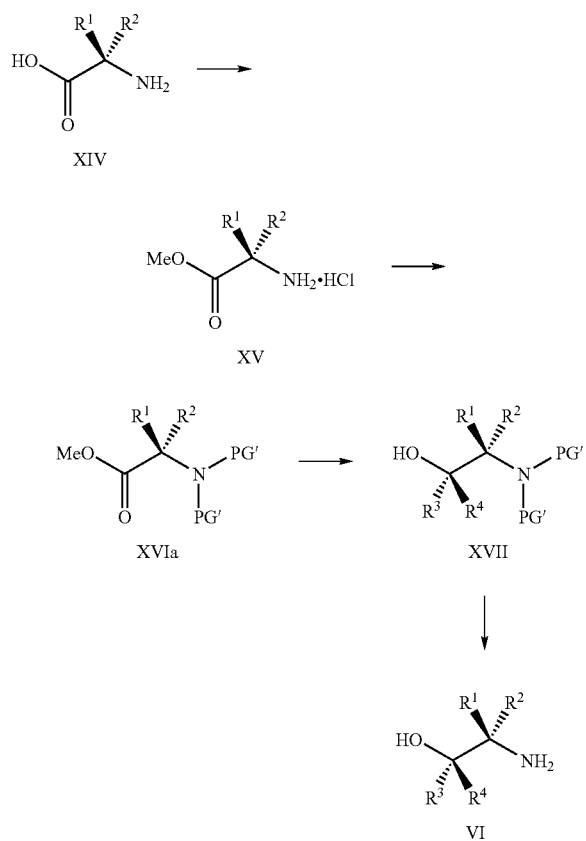

(i) reacting a compound of formula XIV with SOCl$_2$ and MeOH to form a compound of formula XV;
(ii) protecting the amino group of said compound of formula XV to form a compound of formula XVIa;
(iii) reacting said compound of formula XVIa with a Grignard reagent R$^3$X", where R$^3$ is as defined in claim 1 and X" is a halide, to form a compound of formula XVII;
(iv) removing protecting groups PG' from said compound of formula XVII to form said compound of formula VI.

Suitable protecting groups PG and PG' will be familiar to those skilled in the relevant art. By way of example, preferably protecting group PG' is a benzyl group, Bn, and protecting group PG is a trityl group.

Further details of the preparation of compounds the present invention are outlined in the accompanying Examples under the heading "Synthesis".

The present invention is further described by way of the following examples.

EXAMPLES

In contrast to roscovitine, the compounds of the present invention contain modified purine C-2 substituents. In particular, the compounds of the invention contain C-2 substituents having a secondary or tertiary alcohol group rather than a primary alcohol group. Without wishing to be bound by theory, it is believed that the presence of such modified C-2 substituents leads to a reduction in the metabolic alcohol-carboxyl conversion.

In order to offset the reduction in aqueous solubility expected as a result of incorporating additional alkyl substituents into the C-2 substituent, the C-6 benzylamino group of roscovitine was replaced with a (pyridin-3-yl)-methylamino group. The accompanying examples demonstrate that this modification is tolerated in terms of biological activity (CDK2/cyclin E or A, CDK1/cyclin B inhibition and antiproliferative effect on human tumour cell line).

Thus, the present invention demonstrates that modification of the purine C-2 and C-6 substituents of roscovitine affords novel compounds with enhanced therapeutic utility. Indeed, it has been shown that placement of one or two lower alkyl substituents at the carbinol C of the purine C-2 substituent present in roscovitine is not only tolerated in terms of retaining the desired biological activity (potency and selectivity of protein kinase inhibition; cytotoxicity), but in some cases provides more potent compounds. Moreover, the inclusion of a (pyridin-3-yl)-methylamino group in place of the benzylamino group ensures improved hydrophilicity and aqueous solubility profiles for the compounds of this invention compared to roscovitine (calculated n-octanol/water partition coefficients: $2.5 < C \log P < 3.8$ compared to $C \log P = 3.7$ for roscovitine). Furthermore, selected compounds exemplified herein have been shown to possess enhanced resistance to metabolic degradation using an appropriate in vitro model system.

Synthesis

The compounds of general structure 1 can be prepared by methods known in the art (reviewed in Fischer, P. M., and Lane, D. P. Curr. Med. Chem. 2001, 7, 1213-1245). A convenient synthetic route is shown below in Scheme 1 and starts with commercially available 2,6-dichloropurine (2, X=Cl) or 2-amino-6-chloropurine (2, X=NH$_2$). In the latter case, the amino group is transformed to provide the particularly suitable 6-chloro-2-fluoro-purine starting material (2, X=F; Gray, N. S., Kwon, S., and Schultz, P. G. Tetrahedron Lett. 1997, 38, 1161-1164.). Selective amination at the more reactive C-6 position with the appropriate pyridylmethylamine 3 then affords intermediate 4. This is alkylated at the N-9 position, e.g. by nucleophilic substitution using the appropriate alkyl halide R$^5$—X. The product 5 is finally aminated with a hydroxyethylamine 6 at elevated temperature.

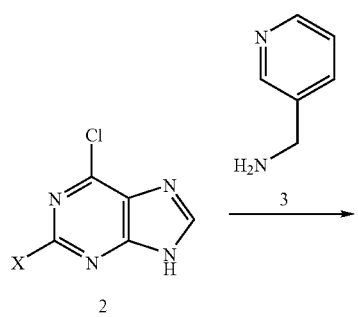

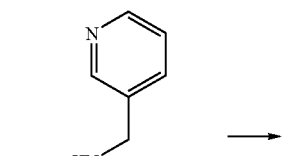

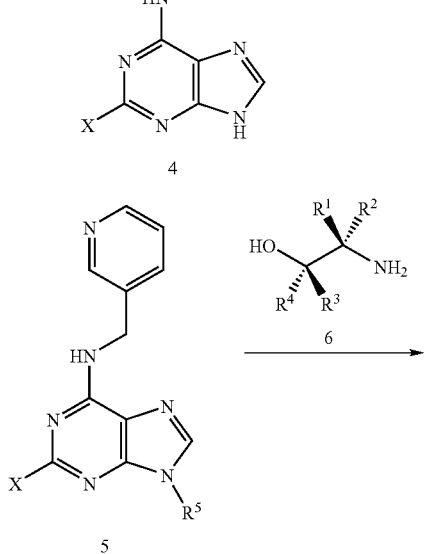

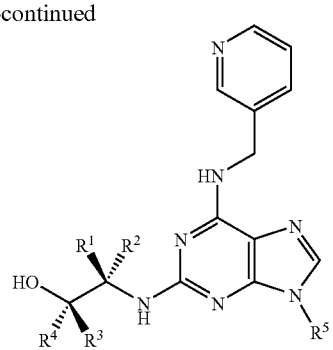

Substituted amino alcohols 6 ($R^1$ or $R^2 <>H$) can be synthesized from α-amino alcohols 7 ($R^1$ or $R^2 <>H$) as shown below in Scheme 2. Many of the latter are available commercially; alternatively, they can be prepared readily by reduction of the corresponding α-amino acids. The initial reaction in the synthetic methodology adopted was trityl protection of the amino function to afford intermediate 8 ($R^1$ or $R^2 <>H$; Evans, P. A., Holmes, A. B., and Russell, K. *J. Chem. Soc., Perkin Trans.* 1, 1994, 3397-3409). This was submitted to Swern oxidation to the corresponding aldehyde 9 ($R^1$ or $R^2 <>H$; Takayama, H., Ichikawa, T., Kuwajima, T., Kitajima, M., Seki, H., Aimi, N., and Nonato, M. G. *J. Am. Chem. Soc.* 2000, 122, 8635-8639). Introduction of the substituent $R^3$ (if $R^2 <>H$) or $R^4$ (if $R^1 <>H$) was accomplished via chelation-controlled alkylation (Reetz, M. T., Roelfing, K., and Griebenow, N. *Tetrahedron Lett.* 1994, 35, 1969-1972) using the appropriate alkyllithium reagent and a copper bromide/dimethyl sulfide complex catalyst in diethyl ether. Depending on the substituent to be introduced, this procedure afforded intermediates 10 in diastereomeric excess (de) of 50-80%. Alternatively, achiral methods can be used, optionally followed by separation/resolution of the optical isomers. For production of amino alcohols where both $R^3$ and $R^4$ are other than H, intermediate 10 was subjected to another Swern oxidation reaction to the respective ketone 12, followed by introduction of the second substituent through alkylation. The final step in the synthesis for all the amino alcohols was removal of the trityl group using trifluoroacetic acid to afford 6 or 11.

Scheme 2

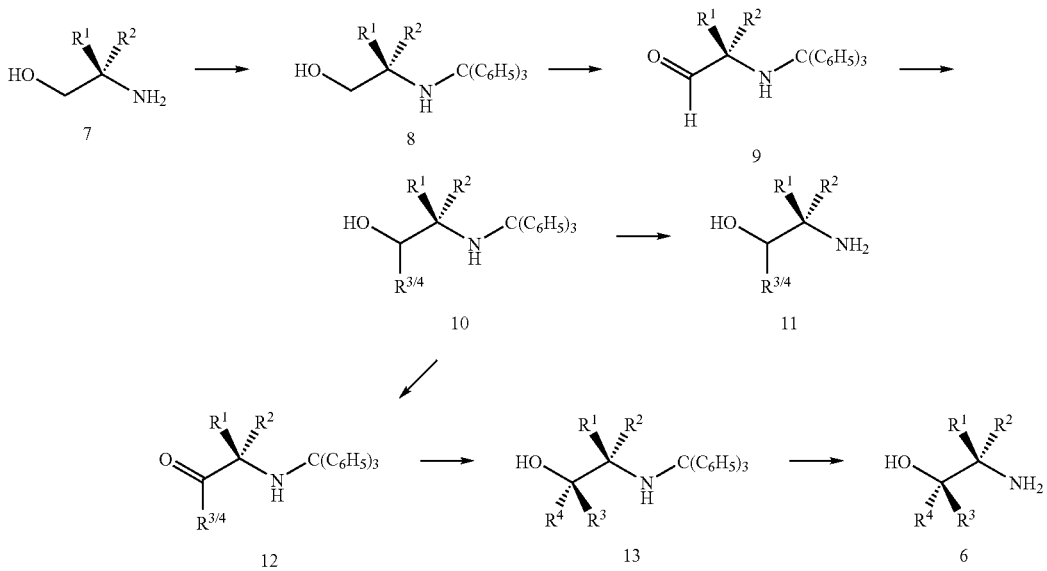

In those cases where amino alcohols contain two identical substituents at the carbinol C (6, $R^1$ or $R^2<>H$; $R^3=R^4$, not H), these can be obtained directly from a suitable corresponding α-amino acid ester, e.g. by double Grignard alkylation (Guenther, B. R., and Kirmse, W. *Liebigs Ann. Chem.* 1980, 518-532).

Kinase Assays

The compounds from the examples below were investigated for their CDK2/cyclin E, CDK1/cyclin B, CDK4/cyclin D1 and CDK7/cyclin H, ERK-2, and PKA inhibitory activity. $His_6$-tagged recombinant human cyclin-dependent kinases CDK1/cyclin B1, CDK2/cyclin E, CDK4 and CDK7/cyclin H were expressed in sf9 cells using a baculovirus expression system. Recombinant cyclin D1 was expressed in *E. coli*. Proteins were purified by metal chelate affinity chromatography to greater than 90% homogeneity. Kinase assays were performed in 96-well plates using recombinant CDK/cyclins, recombinant active ERK-2 (Upstate Biotechnology), or cyclic AMP-dependent kinase (PKA) catalytic subunit (Calbiochem Cat. 539487). Assays were performed in assay buffer (25 mM β-glycerophosphate, 20 mM MOPS, 5 mM EGTA, 1 mM DTT, 1 mM $Na_3VO_3$, pH 7.4), into which were added 2-4 μg of active enzyme with appropriate substrates (purified histone H1 for CDK2, recombinant GST-retinoblastoma protein (residues 773-928) for CDK4, biotinyl-Ahx-(Tyr-Ser-Pro-Thr-Ser-Pro-Ser)$_4$ peptide for CDK7, myelin basic protein for ERK-2, or peptide Kemptide (Fluka Biochemika Cat. 60645) for PKA). The reaction was initiated by addition of Mg/ATP mix (15 mM $MgCl_2$+100 μM ATP with 30-50 kBq per well of $[\gamma\text{-}^{32}P]$-ATP) and mixtures incubated for 10 min (CDK2/cyclin E, ERK-2, PKA) or 45 min (CDK4/cyclin D1, CDK7/cyclin H) as required, at 30° C. Reactions were stopped on ice, followed by filtration through p81 filterplates or GF/C filterplates (for CDK4) (Whatman Polyfiltronics, Kent, UK), except for CDK7 where, after stopping reaction on ice, 10 μL of 10 mg/mL avidin was added to each well and further incubated for 10 min followed by filtration as per CDK2 assay. After washing 3 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (GraphPad Prism version 3.00 for Windows, GraphPad Software, San Diego Calif. USA) to determine $IC_{50}$ values (concentration of test compound which inhibits kinase activity by 50%.). These values for the compounds of the present invention are shown in Table 1.

MTT Cytotoxicity Assay

The compounds from the examples below were subjected to a standard cellular proliferation assay using the following human tumour cell lines: A549, HeLa, HT-29, MCF7, Saos-2, CCRF-CEM, HL-60, and K-562. The cell lines were obtained from the ATCC (American Type Culture Collection, 10801 University Boulevard, Manessas, Va. 20110-2209, USA). Standard 72-h MTT (thiazolyl blue; 3-[4,5-dimethylthiazol-2-yl]-2,5-diphenyltetrazolium bromide) assays were performed (Haselsberger, K.; Peterson, D. C.; Thomas, D. G.; Darling, J. L. Anti Cancer Drugs 1996, 7, 331-8; Loveland, B. E.; Johns, T. G.; Mackay, I. R.; Vaillant, F.; Wang, Z. X.; Hertzog, P. J. Biochemistry International 1992, 27, 501-10). In short: cells were seeded into 96-well plates according to doubling time and incubated overnight at 37° C. Test compounds were made up in DMSO and a ⅓ dilution series prepared in 100 μL cell media, added to cells (in triplicates) and incubated for 72 ho at 37° C. MTT was made up as a stock of 5 mg/mL in cell media and filter-sterilised. Media was removed from cells followed by a wash with 200 μL PBS. MTT solution was then added at 20 μL per well and incubated in the dark at 37° C. for 4 h. MTT solution was removed and cells again washed with 200 μL PBS. MTT dye was solubilised with 200 μL per well of DMSO with agitation. Absorbance was read at 540 nm and data analysed using curve-fitting software (GraphPad Prism version 3.00 for Windows, GraphPad Software, San Diego Calif. USA) to determine $IC_{50}$ values (concentration of test compound which inhibits cell growth by 50%). These values for the compounds of the present invention are shown in Table 2.

Selective Cytotoxicity

Representative compounds of this invention were examined for their anti-proliferative effect against human tumour cell lines and immortalized non-transformed human cell lines ("normal" cell lines). The results are summarized in Table 3. It can be seen that the compounds examined are several-fold more potent anti-proliferative agents compared to roscovitine. Furthermore, their cytotoxic effect is significantly more pronounced against transformed versus non-transformed cell lines.

Comparative In Vitro Metabolism Assay

Microsomal Incubations and Preparation of Samples for Analysis

Microsomes were obtained from Totem Biologicals, Northampton, England. Microsomal protein (0.2 mg) and roscovitine or a test compound of this invention (final concentration 10 μM) were mixed in phosphate-buffered saline (100 μL) containing NADPH (20 mM), $MgCl_2$ (10 mM), and EDTA (1.5 mM). Samples were incubated for 30 min and the reaction stopped by the addition of ice-cold methanol (300 μL) containing olomoucine (Vesely, J., Havlicek, L., Strnad, M., Blow, J. J., Donella-Deana, A., Pinna, L., Letham, D. S., Kato, J., Detivaud, L., Leclerc, S., Meijer, L. *Eur. J. Biochem.* 1994, 224, 771-786) as internal standard. Calibration curves were prepared at 0, 1, and 10 μM in microsomes pre-incubated for 30 min and these were also treated with methanol containing olomoucine. All samples were then centrifuged and the supernatants analysed by liquid chromatography-mass spectrometry.

Liquid Chromatography-Mass Spectrometry

The chromatography column was a Supelco LC-ABZ, 50×4.6 mm, 5 μm zwitterionic column (Supelco Inc., Supelco Park, Bellefonte, Pa., USA). Gradient eluants consisted of methanol (A) and 0.1% formic acid in water (B). The gradient started with 10:90 (A:B v/v) which was held isocratically for 0.5 min, followed by a linear increase to 90:10 (A:B v/v) over 6 min which was then held at these conditions for a further 4 min. The flow rate was 1 mL/min throughout. For LC-UV-MS samples were introduced using a Gilson 215 autosampler (Anachem Ltd., Bedfordshire, UK) attached to a Thermoseparations P4000 quaternary pump, column (as described above) and Thermoseparations UV1000 detector set to 254 nm (Thermoquest Ltd., Hemel Hempstead, Hertfordshire, UK). Eluant from the detector passed, without splitting, into a Thernoquest LCQ ion trap mass spectrometer fitted with an electrospray source operated in positive mode. Mass spectrometer conditions were sheath gas 80, auxiliary gas 20 (both arbitrary units), capillary voltage 4 to 4.5 kV and heated capillary temperature 250 to 280° C. The mass range was 50-750. Scan time was controlled by the ion trap which was set to a maximum ion injection time of 200 ms or the time required to inject $2\times10^8$ ions; for each scan the system automatically used whichever time was reached first.

Data Analysis

To analyse the results selected ion traces of the MH⁺ ions of the test compound and internal standard were extracted and the area of the relevant peaks obtained. The peak area ration (test compound/internal standard) of the test incubation was then compared with the peak area ratios obtained fro the calibration curve of the test compound. From these values the concentration of test compound remaining after 30 min microsomal protein incubation was determined. Results for representative compounds of the present invention are summarized in Table 3, where compound metabolic stability is also compared with that of roscovitine in terms of metabolism (column A), in vitro CDK2 inhibition (column B), and in vitro cytotoxicity on tumour cell lines (column C). Comparative in vitro efficacy (columnd A×C) and cellular exposure (column A×C) are also shown. These results suggest that the compounds of the present invention will have improved in vivo efficacy compared to roscovitine. Calculated n-octanol/water partition coefficients (C log P) are also included in Table 3. It can be seen that those compounds with improved cellular activity and metabolic stability also possess lower C log P than roscovitine, suggesting improved aqueous solubility and thus ease of formulation for drug administration in vivo.

(2R)-2-(6-Benzylamino-9-isopropyl-9H-purin-2-ylamino)-butyric acid

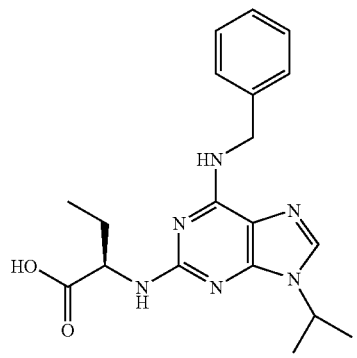 [SMILES: CC[C@@H](Nc1nc(NCc2ccccc2)c2ncn(C(C)C)c2n1)C(=O)O]

Benzyl-(2-fluoro-9-isopropyl-9H-purin-6-yl)-amine (151 mg, 0.5 mmol) was dissolved in NMP (5 mL) and DBU (1.5 mL, 10 mmol). (R)-(−)-2-Aminobutyric acid (99% ee/GLC; 1.03 g, 10 mmol) was then added and the mixture was stirred under $N_2$ at 160° C. for 1 h. After cooling, the mixture was diluted with citric acid (10% aq solution) and $CH_2Cl_2$ (25 mL each). The phases were separated and the organic fraction was extracted with brine (2×10 mL), dried over $MgSO_4$, filtered, and evaporated. The residue was redissolved in MeCN and was fractionated by preparative RP-HPLC (Vydac 218TP1022, 9 mL/min, 22.5-32.5% MeCN in $H_2O$ containing 0.1% $CF_3COOH$ over 40 min). Appropriate fractions were pooled and lyophilised to afford the pure title compound (137 mg, 74.4%) as an amorphous off-white solid. Anal. RP-HPLC (Vydac 218TP54, 1 mL/min): $t_R$=16.04 min (0-60% MeCN), 15.95 min (22.5-32.5% MeCN in $H_2O$ containing 0.1% $CF_3COOH$ over 20 min), purity: >98% ($\lambda$=214 nm). ¹H-NMR ($d_6$-DMSO, 300 MHz) δ: 0.95 (t, J=7.3 Hz, 3H, $CH_2\underline{CH_3}$); 1.51 (d, J=6.7 Hz, 6H, CH($\underline{CH_3}$)$_2$); 1.78 (m, J=7.3 Hz, 2H, $\underline{CH_2}CH_3$); 4.27 (m, 1H, C$\underline{H}$CH2); 4.64 (hept., J=6.7 Hz, 1H, C$\underline{H}$(CH$_3$)$_2$); 4.69 (m, 2H, $\underline{CH_2}$Ph); 7.25-7.41 (m, 6H, ArH). DE-MALDI-TOF MS (α-cyano-4-hydroxy-cinnamic acid matrix): [M+H]⁺=369.41. FAB-MS: [M+H]⁺=369.2033 ($C_{19}H_{25}N_6O_2$ requires 369.2039).

(R)-2-(Trityl-amino)-butan-1-ol

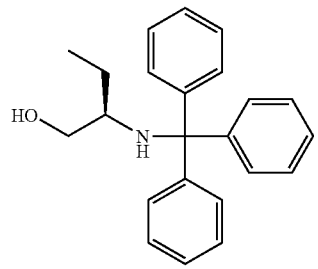

To a stirred solution of (R)-(−)-2-aminobutan-1-ol (10 g, 1 eq, 112.18 mmol) in DCM (500 mL) under an argon atmosphere at room temperature, was added DIEA (30 mL, 1.54 eq, 172.22 mmol) followed by trityl chloride (35.4 mL, 1.13 eq, 126.98 mmol). The reaction mixture was stirred at room temperature for 48 h, when TLC (hexane:ether:MeOH; 55:40:5) indicated that the reaction had gone to completion. The solvent was evaporated in vacuo and the residue precipitated from acetone (50 mL) with hexane (900 mL) with stirring, the precipitate was removed by filtration and the filtrate was evaporated in vacuo. The residue was dissolved in hexane (1 L), filtered, and the filtrate was evaporated in vacuo to afford the title compound as a light yellow oil. Yield: 32 g (86%). ¹H-NMR ($d_6$-DMSO, 250 MHz): δ 0.56 (t, 3H, J=7.41 Hz, —NHCH($CH_2\underline{CH_3}$)$CH_2$OH), 1.10 (m, 2H, —NHCH($\underline{CH_2}CH_3$)$CH_2$OH), 2.22 (m, 1H, —NHCH($CH_2CH_3$)$CH_2$ O$\underline{H}$), 2.38 (m, 1H, —NHC$\underline{H}$($CH_2CH_3$)$CH_2$OH), 2.72+3.00 (2×m, 2H, —NHCH($CH_2CH_3$)$\underline{CH_2}$OH), 4.28 (t, 1H, J=5.26 Hz, —$\underline{NH}$CH($CH_2CH_3$)$CH_2$OH), 7.14-7.49 (m, 15H, 3×Ph).

(S)-2-(Trityl-amino)-butan-1-ol

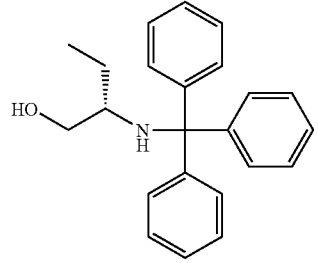 [SMILES: CC[C@@H](CO)NC(c1ccccc1)(c1ccccc1)c1ccccc1]

To a stirred solution of (S)-(+)-2-aminobutan-1-ol (10 g, 1 eq, 112.18 mmol) in DCM (500 mL) under an argon atmosphere at room temperature, was added DIEA (30 mL, 1.54 eq, 172.22 mmol) followed by trityl chloride (35.4 mL, 1.13 eq, 126.98 mmol). The reaction mixture was stirred at this temperature for 48 h, when TLC (hexane:ether:MeOH; 55:40:5) indicated that the reaction had gone to completion. The solvent was evaporated in vacuo and the residue precipitated from acetone (50 mL) with hexane (900 mL) with stirring, the precipitate was removed by filtration and the filtrate was evaporated in vacuo. The residue was dissolved in hexane (1 L), filtered, and the filtrate was evaporated in vacuo to afford the title compound as a light yellow oil. Yield: 33 g (89%). ¹H-NMR (d₆-DMSO, 250 MHz): δ 0.58 (t, 3H, J=7.26 Hz, —NHCH(CH₂CH₃)CH₂OH), 1.10 (m, 2H, —NHCH(CH₂CH₃)CH₂OH), 2.24 (m, 1H, —NHCH(CH₂CH₃)CH₂OH), 2.39 (m, 1H, —NHCH(CH₂CH₃)CH₂OH), 2.76 & 3.03 (2×m, 2H, —NHCH(CH₂CH₃)CH₂OH), 4.32 (t, 1H, J=4.97 Hz, —NHCH(CH₂CH₃)CH₂OH), 7.15-7.52 (m, 15H, 3×Ph).

(R)-2-(Trityl-amino)-butyraldehyde

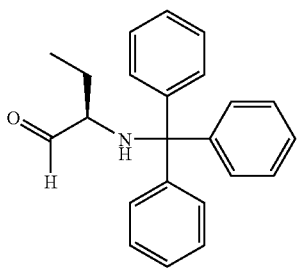

To a stirred solution of DMSO (3.0 mL, 2.8 eq, 42.28 mmol) in DCM (30 mL) under an argon atmosphere at −45° C., was added oxalyl chloride (2 M in DCM, 10.56 mL, 1.40 eq, 21.12 mmol), dropwise. The reaction mixture was stirred at −45° C. for 1 h, after which time a solution of (R)-2-(trityl-amino)-butan-1-ol (5 g, 1 eq, 15.08 mmol) in DCM (30 mL) was added dropwise with stirring. The reaction mixture was stirred at this temperature for 3 h, when TLC (hexane:ether; 80:20) indicated that the reaction had gone to completion. To the reaction mixture was added a solution of TEA (10.5 mL, 5 eq, 75.33 mmol) in DCM (30 mL), and the solution allowed to warm to room temperature over 16 h. The reaction mixture was diluted with more DCM (200 mL) and washed with water (250 mL). The aqueous phase was extracted with DCM (3×50 mL), and the combined organic phase washed with brine (50 mL), dried (MgSO₄) and evaporated in vacuo. The residue was dissolved in ether (30 mL), the solid precipitate removed by filtration and the filtrate was evaporated in vacuo. The residue was dissolved in hexane (50 mL), the solid precipitate removed by filtration and the filtrate was evaporated in vacuo to afford the title compound as a light yellow oil. Yield: 2.59 g (52%). ¹H-NMR (d₆-DMSO, 250 MHz): δ 0.77 (t, 3H, J=7.42 Hz, —NHCH(CH₂CH₃)CHO), 1.34-1.61 (m, 2H, —NHCH(CH₂CH₃)CHO), 2.92 (m, 1H, —NH CH(CH₂CH₃)CHO), 3.62 (d, 1H, J=8.21 Hz, —NH CH(CH₂CH₃)CHO), 7.16-7.46 (m, 15H, 3×Ph), 8.77 (d, 1H, J=3.00 Hz, —NHCH(CH₂CH₃)CHO).

(S)-2-(Trityl-amino)-butyraldehyde

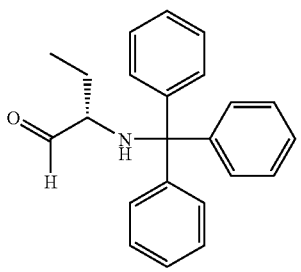

To a stirred solution of DMSO (2.4 mL, 2.8 eq, 33.82 mmol) in DCM (30 mL) under an argon atmosphere at −45° C., was added oxalyl chloride (2 M in DCM, 8.45 mL, 1.40 eq, 16.9 mmol), dropwise. The reaction mixture was stirred at −45° C. for 1 h, after which time a solution of (S)-2-(trityl-amino)-butan-1-ol (4 g, 1 eq, 12.07 mmol) in DCM (30 mL) was added dropwise with stirring. The reaction mixture was stirred at this temperature for 3 h, when TLC (hexane:ether; 80:20) indicated that the reaction had gone to completion. To the reaction mixture was added a solution of TEA (8.4 mL, 5 eq, 60.27 mmol) in DCM (30 mL), and the solution allowed to warm to room temperature over 16 h. The reaction mixture was diluted with more DCM (100 mL) and washed with water (250 mL). The aqueous phase was extracted with DCM (3×50 mL), and the combined organic phase washed with brine (50 mL), dried (MgSO₄) and evaporated in vacuo. The residue was dissolved in ether (30 mL), the solid precipitate removed by filtration and the filtrate was evaporated in vacuo. The residue was dissolved in hexane (50 mL), the solid precipitate removed by filtration and the filtrate was evaporated in vacuo to afford the title compound as a light yellow oil. Yield: 3.64 g (91%). ¹H-NMR (d₆-DMSO, 250 MHz): δ 0.77 (t, 3H, J=7.42 Hz, —NHCH(CH₂CH₃)CHO), 1.37-1.59 (m, 2H, —NHCH(CH₂CH₃)CHO), 2.93 (m, 1H, —NH CH(CH₂CH₃)CHO), 3.62 (d, 1H, J=5.84 Hz, —NH CH(CH₂CH₃)CHO), 7.16-7.46 (m, 15H, 3×Ph), 8.77 (d, 1H, J=3.00 Hz, —NHCH(CH₂CH₃)CHO).

(2S,3R)-3-(Trityl-amino)-pentan-2-ol

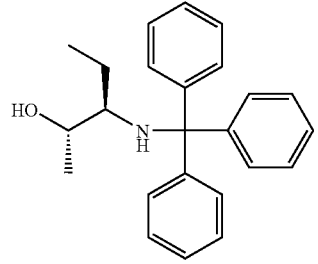 [SMILES: CC[C@@H](NC(c1ccccc1)(c1ccccc1)c1ccccc1)[C@H](C)O]

To a stirred suspension of CuBr.SMe₂ (2.74 g, 2.2 eq, 13.33 mmol) in Et₂O (100 mL) under an argon atmosphere at −70° C., was added methyllithium (1.6 M in Et₂O, 16.6 mL, 4.4 eq, 26.56 mmol) dropwise, and the solution allowed to warm to room temperature. The mixture was recooled to −70° C., to which was added a solution of (R)-2-(trityl-amino)-butyraldehyde (2 g, 1 eq, 6.05 mmol) in Et₂O (25 mL) dropwise with stirring. The reaction mixture was stirred at this temperature for 2 h, when TLC (hexane:ether; 80:20) indicated that the reaction had gone to completion. To the reaction mixture was added a saturated aqueous solution of NH₄Cl (100 mL) and allowed to warm to room temperature over 16 h. The reaction mixture was extracted with ether (2×200 mL), and the combined organic phase washed with brine (50 mL), dried (MgSO₄) and evaporated in vacuo. The residue was purified by silica gel column chromatography, eluted with hexane:ether (80:20) to afford the title compound as a light yellow oil. Yield: 1.91 g (91%). (80% de 2S,3R: 20% de 2R,3R). ¹H-NMR (d₆-DMSO, 250 MHz): δ 0.47 & 0.55 (2×t, J=7.43 & 7.27 Hz, —NHCH(CH₂CH₃)CH(CH₃)OH), 0.99-1.12 (m, 5H, —NHCH(CH₂CH₃)CH(CH₃)OH), 2.03 (m, 1H, —NH CH(CH₂CH₃)CH(CH₃)OH), 3.32-3.51 (m, 1H, —NHCH (CH₂CH₃) CH(CH₃)OH), 4.40 (d, 1H, J=3.79 Hz, —NHCH(CH₂CH₃)CH(CH₃)OH), 7.14-7.51 (m, 15H, 3×Ph).

(2R,3S)-3-(Trityl-amino)-pentan-2-ol

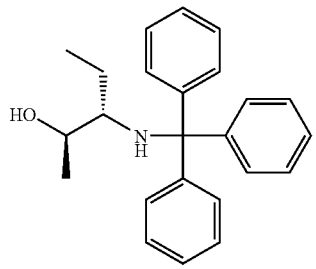 [SMILES: CC[C@H](NC(c1ccccc1)(c1ccccc1)c1ccccc1)[C@@H](C)O]

To a stirred suspension of CuBr.SMe₂ (2.74 g, 2.2 eq, 13.33 mmol) in ether (100 mL) under an argon atmosphere at −70° C., was added methyl lithium (1.6 M in ether, 15.13 mL, 4.0 eq, 24.21 mmol) dropwise and the solution allowed to warm to room temperature. The mixture was recooled to −70° C., to which was added a solution of (S)-2-(trityl-amino)-butyraldehyde (2 g, 1 eq, 6.05 mmol) in Et₂O (25 mL) dropwise with stirring. The reaction mixture was stirred at this temperature for 2 h and then at −55° C. for 4 h, when TLC (hexane:Et₂O; 80:20) indicated that the reaction had gone to completion. To the reaction mixture was added a saturated aqueous solution of NH₄Cl (100 mL) and allowed to warm to room temperature over 16 h. The reaction mixture was extracted with Et₂O (2×200 mL), and the combined organic phase washed with brine (50 mL), dried (MgSO₄) and evaporated in vacuo. The residue was purified by silica gel column chromatography, eluted with hexane:Et₂O (80:20) to afford the title compound as a light yellow oil. Yield: 1.37 g (66%). (80% de 2R,3S: 20% de 2S,3S). ¹H-NMR (d₆-DMSO, 250 MHz): δ 0.0.47 & 0.55 (2×t, J=7.50 & 7.26 Hz —NHCH(CH₂CH₃)CH(CH₃)OH), 0.99-1.12 (m, 5H, —NHCH(CH₂CH₃)CH(CH₃OH), 2.01 (m, 1H, —NHCH(CH₂CH₃)CH(CH₃)OH), 3.22-3.43 (m, 1H, —NHCH(CH₂CH₃) CH(CH₃)OH), 4.41 (d, 1H, J=3.31 Hz, —NHCH(CH₂CH₃)CH(CH₃)OH), 7.14-7.56 (m, 15H, 3×Ph).

(3RS,4R)-4-(Trityl-amino)-hexan-3-ol

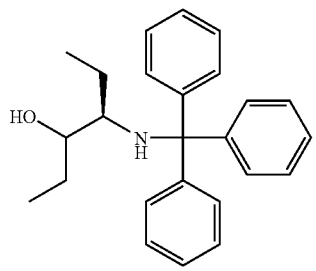

To a stirred solution of (R)-2-(trityl-amino)-butyraldehyde (1.5 g, 1 eq, 4.53 mmol) in Et₂O (150 mL) under an argon atmosphere at −78° C., was added ethylmagnesium bromide (3 M in Et₂O, 1.51 mL, 1 eq, 4.53 mmol) dropwise. The solution was stirred at −78° C. for 2 h, then allowed to warm to room temperature over 16 h. The mixture was recooled to 0° C., H₂O (150 mL) added, and the organic phase separated. The aqueous phase was extracted with more Et₂O (2×50 mL), and the combined organic phase washed with brine (50 mL), dried (MgSO₄) and evaporated in vacuo. The residue was purified by silica gel column chromatography, eluted with hexane:ether (90:10) to afford the title compound as a light yellow oil. Yield: 1.13 g (69%). (57% de 3S,4R: 43% de 3R,4R). ¹H-NMR (d₆-DMSO, 250 MHz): δ 0.45 & 0.69 (t & m, 6H, J=7.43 Hz, —NHCH(CH₂CH₃)CH(CH₂CH₃)OH), 1.12-1.29 (m, 4H, —NHCH(CH₂CH₃)CH (CH₂CH₃)OH), 2.16 (m, 1H, —NHCH(CH₂CH₃)CH(CH₂CH₃)OH), 2.54 (m, 1H, —NHCH(CH₂CH₃)CH(CH₂CH₃)OH), 3.21-3.40 (m, 1H, —NHCH(CH₂CH₃)CH(CH₂CH₃)OH), 4.29+4.39 (2×d, 1H, J=4.42 & 5.37 Hz, —NHCH(CH₂CH₃)CH (CH₂CH₃)OH), 7.15-7.52 (m, 15H, 3×Ph).

(3RS,4S)-4-(Trityl-amino)-hexan-3-ol

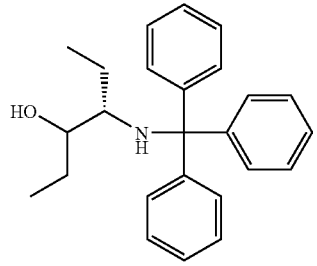 [SMILES: CCC(O)[C@H](CC)NC(c1ccccc1)(c1ccccc1)c1ccccc1]

To a stirred solution of (R)-2-(trityl-amino)-butyraldehyde (1.5 g, 1 eq, 4.53 mmol) in Et₂O (150 mL) under an argon atmosphere at −78° C., was added ethylmagnesium bromide (3 M in Et₂O, 1.51 mL, 1 eq, 4.53 mmol) dropwise. The solution was stirred at −78° C. for 2 h, then allowed to warm to room temperature over 16 h. The mixture was recooled to 0° C., H₂O (150 mL) added, and the organic phase separated. The aqueous phase was extracted with more Et₂O (2×50 mL), and the combined organic phase washed with brine (50 mL), dried (MgSO₄) and evaporated in vacuo. The residue was purified by silica gel column chromatography, eluted with hexane:ether (90:10) to afford the title compound as a light yellow oil. Yield: 1.19 g (73%). (65% de 3R,4S: 35% de 3S,4S). ¹H-NMR (d₆-DMSO, 250 MHz): δ 0.46+0.69 (t & m, 6H, J=7.34 Hz, —NHCH(CH₂CH₃)CH(CH₂CH₃)OH), 1.13-1.29 (m, 4H, —NHCH(CH₂CH₃)CH(CH₂CH₃)OH), 2.17 (m, 1H, —NHCH(CH₂CH₃)CH(CH₂CH₃)OH), 2.55 (m, 1H, —NHCH(CH₂CH₃)CH(CH₂CH₃)OH), 3.20-3.39 (m, 1H, —NHCH(CH₂CH₃)CHCH₂CH₃)OH), 4.29 & 4.39 (2×d, 1H, J=4.74 & 5.53 Hz, —NHCH(CH₂CH₃)CH(CH₂CH₃)OH), 7.15-7.52 (m, 15H, 3×Ph).

(3RS,4R)-2-Methyl-4-(trityl-amino)-hexan-3-ol

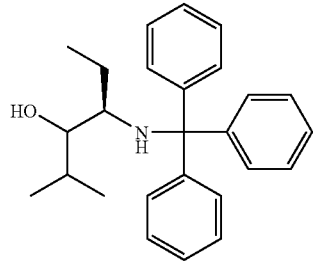 [SMILES: CC[C@@H](NC(c1ccccc1)(c1ccccc1)c1ccccc1)C(O)C(C)C]

To a stirred suspension of CuBr.SMe₂ (1.37 g, 2.2 eq, 6.66 mmol) in Et₂O (100 mL) under an argon atmosphere at −78°

C., was added isopropyllithium (0.7 M in pentane, 17.29 mL, 4 eq, 12.1 mmol) dropwise, and the solution allowed to warm to room temperature. The mixture was recooled to −70° C., to which was added a solution of (R)-2-(trityl-amino)-butyraldehyde (1 g, 1 eq, 3.03 mmol) in Et₂O (25 mL) dropwise with stirring. The reaction mixture was stirred at this temperature for 1 h, then allowed to warm to −55° C. and stirred at this temperature for 3 h. To the reaction mixture was added a saturated aqueous solution of NH₄Cl (100 mL) and allowed to warm to room temperature over 16 h. The reaction mixture was extracted with Et₂O (2×200 mL), and the combined organic phase washed with brine (50 mL), dried (MgSO₄) and evaporated in vacuo. The residue was purified by silica gel gradient column chromatography, eluted with hexane:ether (100:0→90:10) to afford the title compound as a colourless oil. Yield: 0.53 g (47%). (50% de 3S,4R: 50% de 3R,4R) ¹H-NMR (d₆-DMSO, 250 MHz): δ 0.44 (t, 3H, J=7.03 Hz, —NHCH(CH₂C$\underline{H}$₃)CH(CH(CH₃)₂)OH), 0.52 & 0.77 (2×d, 6H, J=6.48 Hz, —NHCH(CH₂CH₃)CH(CH(C$\underline{H}$₃)₂)OH), 0.79-1.13 (m, 2H, —NHCH(C$\underline{H}$₂CH₃)CH(CH(CH₃)₂)OH), 1.72 (m, 1H, —NHCH(CH₂CH₃)CH(CH (CH₃)₂)O$\underline{H}$), 2.11 (m, 1H, —NHC$\underline{H}$(CH₂CH₃)CH(CH(CH₃)₂)OH), 2.77 (m, 1H, —NH CH(CH₂CH₃)CH(C$\underline{H}$(CH₃)₂)OH), 2.99 (m, 1H, —NHCH(CH₂CH₃)C$\underline{H}$(CH(CH₃)₂)OH), 4.55 (d, 1H, J=5.21 Hz, —N$\underline{H}$CH(CH₂CH₃)CH(CH(CH₃)₂)OH), 7.15-7.46 (m, 15H, 3×Ph).

(3RS,4S)-2-Methyl-4-(trityl-amino)-hexan-3-ol

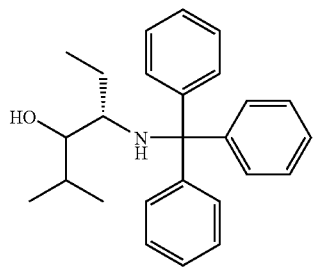 [SMILES: CC[C@H](NC(c1ccccc1)(c1ccccc1)c1ccccc1)C(O)C(C)C]

To a stirred suspension of CuBr.SMe₂ (1.37 g, 2.2 eq, 6.66 mmol) in Et₂O (100 mL) under an argon atmosphere at −78° C., was added isopropyllithium (0.7 M in pentane, 17.29 mL, 4 eq, 12.1 mmol) dropwise and the solution allowed to warm to room temperature. The mixture was recooled to −70° C., to which was added a solution of (S)-2-(trityl-amino)-butyraldehyde (1 g, 1 eq, 3.03 mmol) in Et₂O (25 mL) dropwise with stirring. The reaction mixture was stirred at this temperature for 1 h, then allowed to warm to −55° C. and stirred at this temperature for 3 h. To the reaction mixture was added a saturated aqueous solution of NH₄Cl (100 mL) and allowed to warm to room temperature over 16 h. The reaction mixture was extracted with Et₂O (2×200 mL), and the combined organic phase washed with brine (50 mL), dried (MgSO₄) and evaporated in vacuo. The residue was purified by silica gel column chromatography, eluted with hexane:ether (100:0→90:10) to afford the title compound as a colourless oil; Yield: 0.36 g (32%). (50% de 3R,4S: 50% de 3S,4S). ¹H-NMR (d₆-DMSO, 250 MHz): δ 0.44 (t, 3H, J=6.79 Hz, —NHCH(CH₂C$\underline{H}$₃)CH(CH(CH₃)₂)OH), 0.52 & 0.76 (2×d, 6H, J=6.63 Hz, —NHCH(CH₂CH₃)CH(CH(C$\underline{H}$₃)₂)OH), 0.80-1.15 (m, 2H, —NHCH(C$\underline{H}$₂CH₃)CH(CH(CH₃)₂)OH), 1.70 (m, 1H, —NHCH(CH₂CH₃)CH(CH (CH₃)₂)O$\underline{H}$), 2.10 (m, 1H, —NHC$\underline{H}$(CH₂CH₃)CH(CH(CH₃)₂)OH), 2.76 (m, 1H, —NHCH(CH₂CH₃)C$\underline{H}$(CH(CH₃)₂)OH), 2.99 (m, 1H, —NHCH(CH₂CH₃)CH(C$\underline{H}$(CH₃)₂)OH), 4.55 (d, 1H, J=5.84 Hz, —N$\underline{H}$CH(CH₂CH₃)CH(CH(CH₃)₂)OH), 7.17-7.46 (m, 15H, 3×Ph).

(3RS,4R)-2,2-Dimethyl-4-(trityl-amino)-hexan-3-ol

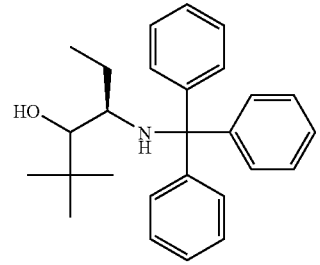 [SMILES: CC[C@@H](NC(c1ccccc1)(c1ccccc1)c1ccccc1)C(O)C(C)(C)C]

To a stirred suspension of CuBr.SMe₂ (1.37 g, 2.2 eq, 6.66 mmol) in Et₂O (100 mL) under an argon atmosphere at −78° C., was added tert-butyllithium (1.5 M in pentane, 8.0 mL, 4 eq, 12.0 mmol) dropwise and the solution allowed to warm to room temperature. The mixture was recooled to −55° C., to which was added a solution of (R)-2-(trityl-amino)-butyraldehyde (1 g, 1 eq, 3.03 mmol) in Et₂O (25 mL) dropwise with stirring, and stirred at this temperature for 3 h. To the reaction mixture was added a saturated aqueous solution of NH₄Cl (100 mL) and allowed to warm to room temperature over 16 h. The reaction mixture was extracted with Et₂O (2×200 mL), and the combined organic phase washed with brine (50 mL), dried (MgSO₄) and evaporated in vacuo. The residue was purified by silica gel gradient column chromatography, eluted with hexane:ether (100:0→90:10) to afford the title compound as a light yellow oil. Yield: 0.57 g (49%). (55% de 3S,4R: 45% de 3R,4R). ¹H-NMR (d₆-DMSO, 250 MHz): δ 0.36 & 0.86 (2×t, 3H, J=7.42 Hz, —NHCH(CH₂C$\underline{H}$₃)CH(C(CH₃)₃)OH), 0.57 & 0.71 (2×s, 9H, —NHCH(CH₂CH₃)CH(C(C$\underline{H}$₃)₃)OH), 1.38-1.52 (m, 2H, —NHCH(C$\underline{H}$₂CH₃)CH(C(CH₃)₃)OH), 1.99 (m, 1H, —NHCH(CH₂CH₃)CH(C(CH₃)₃)O$\underline{H}$), 2.27 (m, 1H, —NH C$\underline{H}$(CH₂CH₃)CH(C(CH₃)₃)OH), 2.95 (m, 1H, —NHCH(CH₂CH₃)C$\underline{H}$(C(CH₃)₃)OH), 4.22 & 4.77 (2×d, 1H, J=4.42 5.21 Hz, —N$\underline{H}$CH(CH₂CH₃)CH(C(CH₃)₃)OH), 7.14-7.52 (m, 15H, 3×Ph).

(3RS,4S)-2,2-Dimethyl-4-(trityl-amino)-hexan-3-ol

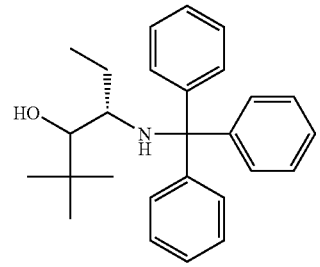 [SMILES: CC[C@H](NC(c1ccccc1)(c1ccccc1)c1ccccc1)C(O)C(C)(C)C]

To a stirred suspension of CuBr.SMe₂ (1.37 g, 2.2 eq, 6.66 mmol) in Et₂O (100 mL) under an argon atmosphere at −78° C., was added tert-butyl lithium (1.5 M in pentane, 8.0 mL, 4 eq, 12.0 mmol) dropwise and the solution allowed to warm to room temperature. The mixture was recooled to −55° C., to which was added a solution of (S)-2-(trityl-amino)-butyraldehyde (1 g, 1 eq, 3.03 mmol) in Et$_2$O (25 mL) dropwise with stirring, and stirred at this temperature for 3 h. To the reaction mixture was added a saturated aqueous solution of NH$_4$Cl (100 mL) and allowed to warm to room temperature over 16 h. The reaction mixture was extracted with Et$_2$O (2×200 mL), and the combined organic phase washed with brine (50 mL), dried (MgSO$_4$) and evaporated in vacuo. The residue was purified by silica gel column chromatography, eluted with hexane: Et$_2$O (100:0→90:10) to afford the title compound as a light yellow oil. Yield: 0.47 g (40%). (53% de 3R,4S: 47% de 3S,4S). $^1$H-NMR (d$_6$-DMSO, 250 MHz): δ 0.37 & 0.87 (2×t, 3H, J=7.46 Hz, —NHCH(CH$_2$CH$_3$)CH(C(CH$_3$)$_3$)OH), 0.58 & 0.71 (2×s, 9H, —NHCH(CH$_2$CH$_3$)CH(C(CH$_3$)$_3$)OH), 1.38-1.52 (m, 2H, —NHCH(CH$_2$ CH$_3$)CH(C(CH$_3$)$_3$)OH), 2.00 (m, 1H, —NHCH(CH$_2$CH$_3$)CH(C(CH$_3$)$_3$)OH), 2.28 (m, 1H, —NHCH(CH$_2$CH$_3$)CH(C(CH$_3$)$_3$)OH), 2.95 (m, 1H, —NHCH(CH$_2$CH$_3$)CH(C(CH$_3$)$_3$)OH), 4.24 & 4.79 (2×d, 1H, J=5.21 & 6.16 Hz, —NH CH(CH$_2$CH$_3$)CH(C(CH$_3$)$_3$)OH), 7.15-7.53 (m, 15H, 3×Ph).

(3R)-3-(Trityl-amino)-pentan-2-one

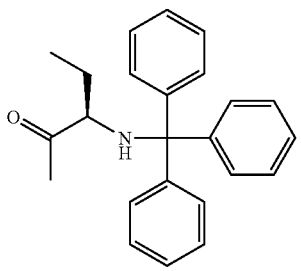 [SMILES: CC[C@@H](NC(c1ccccc1)(c1ccccc1)c1ccccc1)C(C)=O]

To a stirred solution of DMSO (2.19 mL, 2.8 eq, 30.86 mmol) in DCM (30 mL) under an argon atmosphere at −45° C., was added oxalyl chloride (2 M in DCM, 7.69 mL, 1.4 eq, 15.38 mmol) dropwise. The reaction mixture was stirred at −45° C. for 1 h, after which time a solution (2S,3R)-3-(trityl-amino)-pentan-2-ol (3.81 g, 1 eq, 11.04 mmol) in DCM (20 mL) was added dropwise with stirring. The reaction mixture was stirred at this temperature for 4 h, when TLC (hexane: ether; 80:20) indicated that the reaction had gone to completion. To the reaction mixture was added N-ethylpiperidine (7.54 mL, 5 eq, 54.88 mmol), and the solution allowed to warm to room temperature over 16 h. The reaction mixture was diluted with more DCM (50 mL) and washed with water (200 mL). The aqueous phase was extracted with DCM (2×50 mL), and the combined organic phase washed with brine (50 mL), dried (MgSO$_4$) and evaporated in vacuo. The residue was dissolved in Et$_2$O (100 mL), the solid precipitate removed by filtration and the filtrate was evaporated in vacuo. The residue was dissolved in hexane (50 mL), the solid precipitate removed by filtration and the filtrate was evaporated in vacuo to afford the title compound as a light yellow oil. Yield: 3.78 g (100%). $^1$H-NMR (d$_6$-DMSO, 250 MHz): δ 0.73 (t, 3H, J=7.35 Hz, —NHCH(CH$_2$CH$_3$)C(CH$_3$)O), 1.47-1.60 (m, 5H, —NHCH(CH$_2$CH$_3$)C(CH$_3$)O), 3.12 (d, 1H, J=8.38 Hz, —NHCH(CH$_2$CH$_3$)C(CH$_3$)O), 3.32 (m, 1H, —NHCH(CH$_2$CH$_3$) C(CH$_3$)O), 7.16-7.49 (m, 15H, 3×Ph).

(3S)-3-(Trityl-amino)-pentan-2-one

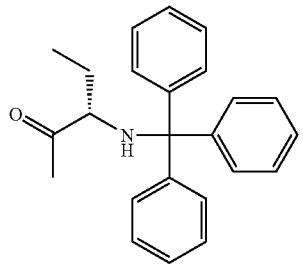

To a stirred solution of DMSO (1.95 mL, 2.8 eq, 27.48 mmol) in DCM (30 mL) under an argon atmosphere at −45° C., was added oxalyl chloride (2 M in DCM, 6.85 mL, 1.4 eq, 13.70 mmol) dropwise. The reaction mixture was stirred at −45° C. for 1 h, after which time a solution (2R,3S)-3-(trityl-amino)-pentan-2-ol (3.39 g, 1 eq, 9.83 mmol) in DCM (20 mL) was added dropwise with stirring. The reaction mixture was stirred at this temperature for 4 h, when TLC (hexane: ether; 80:20) indicated that the reaction had gone to completion. To the reaction mixture was added N-ethylpiperidine (6.71 mL, 5 eq, 48.84 mmol), and the solution allowed to warm to room temperature over 16 h. The reaction mixture was diluted with more DCM (50 mL) and washed with water (200 mL). The aqueous phase was extracted with DCM (2×50 mL), and the combined organic phase washed with brine (50 mL), dried (MgSO$_4$) and evaporated in vacuo. The residue was dissolved in Et$_2$O (100 mL), the solid precipitate removed by filtration and the filtrate was evaporated in vacuo. The residue was dissolved in hexane (50 mL), the solid precipitate removed by filtration and the filtrate was evaporated in vacuo to afford the title compound as a light yellow oil. Yield: 3.15 g (93%). $^1$H-NMR (d$_6$-DMSO, 250 MHz): δ 0.73 (t, 3H, J=7.50 Hz, —NHCH(CH$_2$CH$_3$)C(CH$_3$)O), 1.45-1.62 (m, 5H, —NHCH(CH$_2$CH$_3$)C(CH$_3$)O), 3.12 (d, 1H, J=8.53 Hz, —NHCH(CH$_2$CH$_3$)C(CH$_3$)O), 3.31 (m, 1H, —NH CH(CH$_2$CH$_3$)C(CH$_3$)O), 7.13-7.45 (m, 15H, 3×Ph).

(3R)-2-Methyl-3-(trityl-amino)-pentan-2-ol

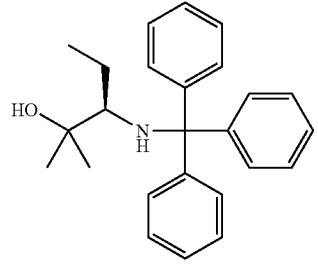 [SMILES: CC[C@@H](NC(c1ccccc1)(c1ccccc1)c1ccccc1)C(C)(C)O]

To a stirred solution of (3R)-3-(trityl-amino)-pentan-2-one (0.87 g, 1 eq, 2.54 mmol) in Et$_2$O (100 mL) under an argon atmosphere at room temperature, was added methylmagnesium iodide (3 M in ether, 2.54 mL, 3 eq, 7.62 mmol) dropwise. The solution was placed in a preheated oil bath at 45° C. and refluxed at this temperature for 16 h. The mixture was recooled to 0° C., H₂O (100 mL) added, the solution filtered through Celite, and the Celite washed with more Et₂O (50 mL). The combined organic phase was separated, the aqueous phase was extracted with Et₂O (2×50 mL), and the combined organic phase washed with brine (50 mL), dried (MgSO₄) and evaporated in vacuo. The residue was purified by silica gel column chromatography, eluted with hexane:ether (100:0→90:10) to afford the title compound as a light yellow oil. Yield: 0.21 g (23%). ¹H-NMR (d₆-DMSO, 250 MHz): δ 0.26 (t, J=7.42 Hz, —NHCH(CH₂C$\underline{H}$₃)CH(CH₃)OH), 1.00 & 1.25 (2×s, 6H, —NHCH(CH₂CH₃)C(C$\underline{H}_3$)₂OH), 0.72-1.43 (m, 2H, —NHCH(C$\underline{H}_2$CH₃)C(CH₃)₂OH), 1.84 (m, 1H, —NHCH(CH₂CH₃)C(CH₃)₂O$\underline{H}$), 2.90 (m, 1H, —NHC$\underline{H}$(CH₂CH₃)C(CH₃)₂OH), 4.32 (s, 1H, —N$\underline{H}$CH(CH₂CH₃)C(CH₃)₂OH), 7.17-7.46 (m, 15H, 3×Ph).

(3S)-2-Methyl-3-(trityl-amino)-pentan-2-ol

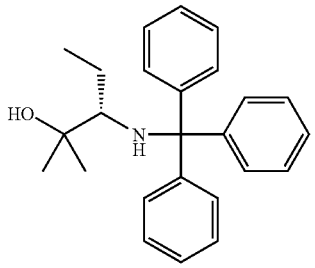 [SMILES: CC[C@H](NC(c1ccccc1)(c1ccccc1)c1ccccc1)C(C)(C)O]

To a stirred solution of (3S)-3-(trityl-amino)-pentan-2-one (0.59 g, 1 eq, 1.72 mmol) in Et₂O (100 mL) under an argon atmosphere at room temperature, was added methylmagnesium iodide (3 M in Et₂O, 1.72 mL, 3 eq, 5.16 mmol) dropwise. The solution was placed in a preheated oil bath at 45° C. and refluxed at this temperature for 16 h. The mixture was recooled to 0° C., H₂O (100 mL) added, the solution filtered through Celite, and the Celite washed with more Et₂O (50 mL). The combined organic phase was separated, the aqueous phase was extracted with Et₂O (2×50 mL), and the combined organic phase washed with brine (50 mL), dried (MgSO₄) and evaporated in vacuo. The residue was purified by silica gel column chromatography, eluted with hexane: Et₂O (100:0→90:10) to afford the title compound as a light yellow oil. Yield: 0.10 g (16%). ¹H-NMR (d₆-DMSO, 250 MHz): δ 0.27 (t, J=7.10 Hz, —NHCH(CH₂C$\underline{H}_3$)CH(CH₃)OH), 0.99 & 1.25 (2×s, 6H, —NHCH(CH₂CH₃)C(C$\underline{H}_3$)₂OH), 0.75-1.42 (m, 2H, —NHCH(C$\underline{H}_2$CH₃)C(CH₃)₂OH), 1.88 (m, 1H, —NHCH(CH₂CH₃)C(CH₃)₂O$\underline{H}$), 2.92 (m, 1H, —NHC$\underline{H}$(CH₂CH₃)C(CH₃)₂OH), 4.32 (s, 1H, —N$\underline{H}$CH(CH₂CH₃)C(CH₃)₂OH), 7.18-7.46 (m, 15H, 3×Ph).

(2S,3R)-3-Amino-pentan-2-ol

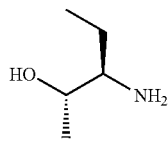

To a stirred solution of (2S,3R)-3-(trityl-amino)-pentan-2-ol (1.32 g, 1 eq, 3.83 mmol) in DCM (50 mL) under an argon atmosphere at room temperature, was added CF₃COOH (10 mL) dropwise, and the solution was stirred at this temperature for 1 h. The solvent was evaporated in vacuo and the residue was precipitated from Et₂O (15 mL) with hexane (300 mL) with stirring to give a yellow oil. The solvent was decanted from the oil, and the oil was washed with hexane (30 mL) and dried in vacuo to afford the title compound as a light yellow oil. Yield: 0.30 g (99%). (80% de 2S,3R: 20% de 2R,3R). ¹H-NMR (d₆-DMSO, 250 MHz): δ 0.915 & 0.924 (2×t, 3H, J=7.50 & 7.58 Hz, NH₂CH(CH₂C$\underline{H}_3$)CH(CH₃)OH), 1.06 & 1.13 (2×d, J=6.48 & 6.32 Hz), NH₂CH (CH₂CH₃)CH (C$\underline{H}_3$)OH), 1.41-1.59 (m, 2H, NH₂CH(C$\underline{H}_2$ CH₃)CH(CH₃) OH), 2.77 & 2.93 (2×m, 1H, NH₂C$\underline{H}$(CH₂CH₃)CH(CH₃)OH), 3.62-3.72 & 3.80-3.90 (2×m, 1H, NH₂CH(CH₂CH₃)C$\underline{H}$(CH₃)OH), 7.75 (bs, 2H, N$\underline{H}_2$).

(2R,3S)-3-Amino-pentan-2-ol

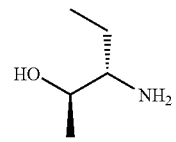

To a stirred solution of (2R,3S)-3-(trityl-amino)-pentan-2-ol (1.64 g, 1 eq, 4.75 mmol) in DCM (50 mL) under an argon atmosphere at room temperature, was added CF₃COOH (10 mL) dropwise, and the solution was stirred at this temperature for 1 h. The solvent was evaporated in vacuo and the residue was precipitated from Et₂O (15 mL) with hexane (300 mL) with stirring to give a yellow oil. The solvent was decanted from the oil, and the oil was washed with hexane (30 mL) and dried in vacuo to afford the title compound as a light yellow oil. Yield: 0.30 g (98%). (80% de 2R,3S: 20% de 2S,3S). ¹H-NMR (d₆-DMSO, 250 MHz): δ 0.913 & 0.923 (2×t, 3H, J=7.50 & 7.50 Hz, NH₂CH(CH₂C$\underline{H}_3$)CH(CH₃)OH), 1.11 & 1.18 (2×d, J=6.48 & 6.48 Hz), NH₂CH(CH₂CH₃)CH (C$\underline{H}_3$)OH), 1.41-1.65 (m, 2H, NH₂CH(C$\underline{H}_2$ CH₃)CH(CH₃) OH), 2.76+2.93 (2×m, 1H, NH₂C$\underline{H}$(CH₂CH₃)CH(CH₃)OH), 3.61-3.69 & 3.80-3.90 (2×m, 1H, NH₂CH(CH₂CH₃) C$\underline{H}$(CH₃)OH), 7.73 (bs, 2H, N$\underline{H}_2$).

(3RS,4R)-4-Amino-hexan-3-ol

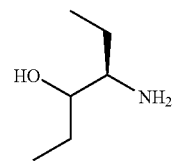

To a stirred solution of (3RS,4R)-4-(trityl-amino)-hexan-3-ol (1.13 g, 1 eq, 3.14 mmol) in DCM (15 mL) under an argon atmosphere at room temperature, was added CF₃COOH (7 mL) dropwise, and the solution was stirred at this temperature for 4 h. The solvent was evaporated in vacuo, EtOH (20 mL) added, and removed in vacuo, and this process repeated twice. The residue was precipitated from Et₂O (5 mL) with hexane (40 mL) with stirring to give a yellow oil. The solvent was decanted from the oil, and the oil was washed with hexane (30 mL) and dried in vacuo to afford the title compound as a light yellow oil. Yield: 0.37 g (100%). (57% de 3S,4R: 43% de 3R,4R). ¹H-NMR (d₆-DMSO, 250 MHz): δ

0.79 & 0.92 (t & m, 6H, J=7.42 Hz, NH₂CH(CH₂CH₃)CH(CH₂CH₃)OH), 1.30-1.67 (m, 4H, NH₂CH(CH₂CH₃)CH(CH₂CH₃)OH), 2.70 (m, 1H, NH₂CH(CH₂CH₃)CH(CH₂CH₃)OH), 2.84 & 2.96 (2×m, 1H, NH₂CH(CH₂CH₃)CH(CH₂CH₃)OH), 3.41 & 3.56 (2×m, 1H, NH₂CH(CH₂CH₃)CH(CH₂CH₃)OH), 7.71 (bs, 2H, NH₂CH(CH₂CH₃)CH(CH₂CH₃)OH).

(3RS,4S)-4-Amino-hexan-3-ol

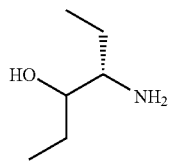

To a stirred solution of (3RS,4S)-4-(trityl-amino)-hexan-3-ol (1.19 g, 1 eq, 3.31 mmol) in DCM (15 mL) under an argon atmosphere at room temperature, was added CF₃COOH (7 mL) dropwise, and the solution was stirred at this temperature for 4 h. The solvent was evaporated in vacuo, EtOH (20 mL) added, and removed in vacuo, and this process repeated twice. The residue was precipitated from Et₂O (5 mL) with hexane (40 mL) with stirring to give a yellow oil. The solvent was decanted from the oil, and the oil was washed with hexane (30 mL) and dried in vacuo to afford the title compound. Yield: 0.39 g (99%). (65% de 3R,4S: 35% de 3S,4S). ¹H-NMR (d₆-DMSO, 250 MHz): δ 0.79 & 0.92 (t & m, 6H, J=7.50 Hz, NH₂CH(CH₂CH₃)CH(CH₂CH₃)OH), 1.22-1.68 (m, 4H, NH₂CH(CH₂CH₃)CH(CH₂CH₃)OH), 2.71 (m, 1H, NH₂CH(CH₂CH₃)CH(CH₂CH₃)OH), 2.83 & 2.95 (2×m, 1H, NH₂CH(CH₂CH₃)CH(CH₂CH₃)OH), 3.39 & 3.54 (2×m, 1H, NH₂CH(CH₂CH₃)CH(CH₂CH₃)OH), 7.77 (bs, 2H, NH₂CH(CH₂CH₃)CH(CH₂CH₃)OH).

(3RS,4R)-4-Amino-2-methyl-hexan-3-ol

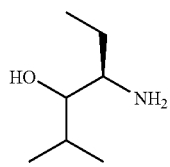

To a stirred solution of (3RS,4R)-2-methyl-4-(trityl-amino)-hexan-3-ol (0.53 g, 1 eq, 1.41 mmol) in DCM (20 mL) under an argon atmosphere at room temperature, was added CF₃COOH (5 mL) dropwise, and the solution was stirred at this temperature for 1 h. The solvent was evaporated in vacuo, the residue was precipitated from Et₂O (10 mL) with hexane (90 mL) with stirring to give a yellow oil. The solvent was decanted from the oil, and the oil was washed with hexane (20 mL) and dried in vacuo to afford the title compound as a light yellow oil. Yield: 0.18 g (100%). (50% de 3S,4R: 50% de 3R,4R). ¹H-NMR (d₆-DMSO, 250 MHz): δ 0.85-0.99 (m, 9H, NH₂CH(CH₂CH₃)CH(CH(CH₃)₂)OH), 1.42-1.79 (m, 2H, NH₂CH(CH₂CH₃)CH(CH(CH₃)₂)OH), 2.95 (m, 1H, NH₂CH(CH₂CH₃)CH(CH(CH₃)₂)OH), 3.18 (m, 1H, NH₂CH(CH₂CH₃)CH(CH(CH₃)₂)OH), 3.37 (m, 1H, NH₂CH(CH₂CH₃)CH(CH(CH₃)₂)OH), 7.58 (bs, 2H, NH₂CH(CH₂CH₃)CH(CH(CH₃)₂)OH).

(3RS,4S)-4-Amino-2-methyl-hexan-3-ol

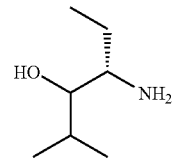

To a stirred solution of (3RS,4S)-2-methyl-4-(trityl-amino)-hexan-3-ol (0.36 g, 1 eq, 0.97 mmol) in DCM (20 mL) under an argon atmosphere at room temperature, was added CF₃COOH (5 mL) dropwise, and the solution was stirred at this temperature for 1 h. The solvent was evaporated in vacuo, the residue was precipitated from Et₂O (10 mL) with hexane (90 mL) with stirring to give a yellow oil. The solvent was decanted from the oil, and the oil was washed with hexane (20 mL) and dried in vacuo to afford the title compound as a light yellow oil. Yield: 0.13 g (100%). (50% de 3R,4S: 50% de 3S,4S) ¹H-NMR (d₆-DMSO, 250 MHz): δ 0.85-1.01 (m, 9H, NH₂CH(CH₂CH₃)CH(CH(CH₃)₂)OH), 1.44-1.76 (m, 2H, NH₂CH(CH₂CH₃)CH(CH(CH₃)₂)OH), 2.94 (m, 1H, NH₂CH(CH₂CH₃)CH(CH(CH₃)₂)OH), 3.17 (m, 1H, NH₂CH(CH₂CH₃)CH(CH(CH₃)₂)OH), 3.40 (m, 1H, NH₂CH(CH₂CH₃)CH(CH(CH₃)₂)OH), 7.54 (bs, 2H, NH₂CH(CH₂CH₃)CH(CH(CH₃)₂)OH).

(3RS,4R)-4-Amino-2,2-dimethyl-hexan-3-ol

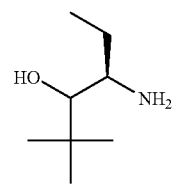

To a stirred solution of (3RS,4R)-2,2-dimethyl-4-(trityl-amino)-hexan-3-ol (0.57 g, 1 eq, 1.47 mmol) in DCM (10 mL) under an argon atmosphere at room temperature, was added CF₃COOH (5 mL) dropwise, and the solution was stirred at this temperature for 1 h. The solvent was evaporated in vacuo, the residue was precipitated from Et₂O (3 mL) with hexane (20 mL) with stirring to give a yellow oil. The solvent was decanted from the oil, and the oil was washed with hexane (20 mL) and dried in vacuo to afford the title compound as a light yellow oil. Yield: 0.21 g (100%). (55% de 3S,4R: 45% de 3R,4R). ¹H-NMR (d₆-DMSO, 250 MHz): δ 0.84-0.99 (m, 3H, NH₂CH(CH₂CH₃)CH(C(CH₃)₃)OH), 1.25-1.29 (m, 9H, NH₂CH(CH₂CH₃)CH(C(CH₃)₃)OH), 1.20-1.72 (m, 2H, NH₂CH(CH₂CH₃)CH(C(CH₃)₃)OH), 3.14 (m, 1H, NH₂CH(CH₂CH₃)CH(C(CH₃)₃)OH), 3.39 (m, 1H, NH₂CH(CH₂CH₃)CH(C(CH₃)₃) OH), 3.65 (m, 1H, NH₂CH(CH₂CH₃)CH(C(CH₃)₃)OH), 7.43, 7.77 & 8.54 (3×bs, 2H, NH₂CH(CH₂CH₃)CH(CH(CH₃)₂)OH).

(3RS,4S)-4-Amino-2,2-dimethyl-hexan-3-ol

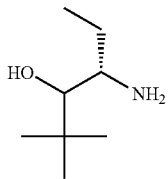

To a stirred solution of (3RS,4S)-2,2-dimethyl-4-(tritylamino)-hexan-3-ol (0.47 g, 1 eq, 1.21 mmol) in DCM (10 mL) under an argon atmosphere at room temperature, was added CF$_3$COOH (5 mL) dropwise, and the solution was stirred at this temperature for 1 h. The solvent was evaporated in vacuo, the residue was precipitated from Et$_2$O (3 mL) with hexane (20 mL) with stirring to give a yellow oil. The solvent was decanted from the oil, and the oil was washed with hexane (20 mL) and dried in vacuo to afford the title compound as a light yellow oil. Yield: 0.18 g (99%). (53% de 3R,4S: 47% de 3S,4S). $^1$H-NMR (d$_6$-DMSO, 250 MHz): δ 0.86-0.99 (m, 3H, NH$_2$CH(CH$_2$CH$_3$)CH(C(CH$_3$)$_3$)OH), 1.25-1.30 (m, 9H, NH$_2$CH(CH$_2$CH$_3$)CH(C(CH$_3$)$_3$)OH), 1.20-1.67 (m, 2H, NH$_2$CH(CH$_2$CH$_3$)CH(C(CH$_3$)$_3$)OH), 3.14 (m, 1H, NH$_2$CH(CH$_2$CH$_3$)CH(C(CH$_3$)$_3$)OH), 3.38 (m, 1H, NH$_2$CH(CH$_2$CH$_3$)CH(C(CH$_3$)$_3$)OH), 3.64 (m, 1H, NH$_2$CH(CH$_2$CH$_3$)CH(C(CH$_3$)$_3$)OH), 7.41, 7.73 & 8.44 (3×bs, 2H, NH$_2$CH(CH$_2$CH$_3$)CH(CH(CH$_3$)$_2$)OH).

(3R)-3-Amino-2-methyl-pentan-2-ol

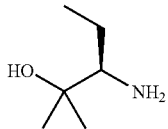

To a stirred solution of (3R)-2-methyl-3-(tritylamino)-pentan-2-ol (0.21 g, 1 eq, 0.60 mmol) in DCM (5 mL) under an argon atmosphere at room temperature, was added CF$_3$COOH (2.5 mL) dropwise, and the solution was stirred at this temperature for 1 h. The solvent was evaporated in vacuo and the residue was precipitated from Et$_2$O (15 mL) with hexane (300 mL) with stirring to give a yellow oil. The solvent was decanted from the oil, and the oil was washed with hexane (30 mL) and dried in vacuo to afford the title compound as a light yellow oil; Yield: 0.07 g (100%). $^1$H-NMR (d$_6$-DMSO, 250 MHz): δ 0.97 (t, 3H, J=7.42 Hz, NH$_2$CH(CH$_2$CH$_3$)C(CH$_3$)$_2$OH), 1.06 & 1.19 (2×s, 6H, NH$_2$CH(CH$_2$CH$_3$)C(CH$_3$)$_2$OH), 1.28-1.71 (m, 2H, NH$_2$CH(CH$_2$CH$_3$)C(CH$_3$)$_2$OH), 2.72 (m, 1H, NH$_2$CH(CH$_2$CH$_3$)C(CH$_3$)$_2$OH), 5.21 (s, 1H, NH$_2$CH(CH$_2$CH$_3$)C(CH$_3$)$_2$OH), 7.63 (bs, 2H, NH$_2$CH(CH$_2$CH$_3$)C(CH$_3$)$_2$OH).

(3S)-3-Amino-2-methyl-pentan-2-ol

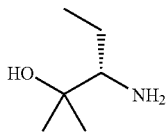

To a stirred solution of (3S)-2-methyl-3-(tritylamino)-pentan-2-ol (0.38 g, 1 eq, 1.06 mmol) in DCM (5 mL) under an argon atmosphere at room temperature, was added CF$_3$COOH (2.5 mL) dropwise, and the solution was stirred at this temperature for 1 h. The solvent was evaporated in vacuo and the residue was precipitated from Et$_2$O (15 mL) with hexane (300 mL) with stirring to give a yellow oil. The solvent was decanted from the oil, and the oil was washed with hexane (30 mL) and dried in vacuo to afford the title compound as a light yellow oil. Yield: 0.12 g (99%). $^1$H-NMR (d$_6$-DMSO, 250 MHz): δ 0.97 (t, 3H, J=7.42 Hz, NH$_2$CH(CH$_2$CH$_3$)C(CH$_3$)$_2$OH), 1.07 & 1.19 (2×s, 6H, NH$_2$CH(CH$_2$CH$_3$)C(CH$_3$)$_2$OH), 1.28-1.61 (m, 2H, NH$_2$CH(CH$_2$CH$_3$)C(CH$_3$)$_2$OH), 2.72 (m, 1H, NH$_2$CH(CH$_2$CH$_3$)C(CH$_3$)$_2$OH), 5.21 (s, 1H, NH$_2$CH(CH$_2$CH$_3$)C(CH$_3$)$_2$OH), 7.63 (bs, 2H, NH$_2$CH(CH$_2$CH$_3$)C(CH$_3$)$_2$OH).

6-Chloro-2-fluoro-9H-purine

This compound was prepared by a modification of a literature procedures (Gray, N. S.; Kwon, S.; Schultz, P. G. *Tetrahedron Lett.* 1997, 38(7), 1161-1164.)

6-Chloro-9H-purin-2-ylamine (75.0 g, 0.44 mol) was suspended in aq HBF$_4$ (1.5 L of 48% w/w solution in H$_2$O). This mixture was cooled to −15° C. and was stirred vigorously. NaNO$_2$ (2.5 L of an 0.3 M aq solution) was then added slowly over 75 min with stirring and careful temperature control (<10° C.). After complete addition, the pale yellow solution was further stirred at room temperature for 30 min. It was then re-cooled to −15° C. and was neutralised carefully to pH=6.2 with NaOH (50% w/v aq solution). This solution was rotary evaporated to semi-dryness. The resulting cake was divided with a spatula and dried under high vacuum overnight. The resulting yellow powder was dry-loaded onto a flash chromatography column (24×15 cm SiO$_2$ bed), which was eluted with CH$_2$Cl$_2$/MeOH, 9:1. Appropriate fractions were collected, pooled, and evaporated. After drying in vacuo, the title compound (34.8 g, 48%) was obtained as a colourless powder. TLC: R$_f$=0.25 (CH$_2$Cl$_2$/MeOH, 9:1), starting material R$_f$=0.16. m/z 173 (MH$^+$, 100), 175 (MH$^{+2}$, 33).

(2-Fluoro-9H-purin-6-yl)-pyridin-3-ylmethyl-amine

To a stirred solution of 6-chloro-2-fluoropurine (0.9 g, 1 eq, 5.22 mmol) in n-BuOH (60 mL) under an argon atmosphere, cooled to −20° C., was added DIEA (2.5 mL, 2.75 eq, 14.35 mmol) followed by C-pyridin-3-yl-methylamine (0.58 mL, 1.1 eq, 5.69 mmol). The reaction mixture was stirred at −20° C. for 3 h, and then allowed to return to room temperature over 2 h, when TLC (CHCl$_3$:MeOH; 90:10) indicated that the reaction had gone to completion. The solvent was evaporated in vacuo and the residue was purified by gradient column chromatography on silica gel, eluted with CHCl$_3$:MeOH (97:3→90:10), to afford the title compound as a white solid. Yield: 1.08 g (85%). Mp 218-220° C. $^1$H-NMR (d$_6$-DMSO, 250 MHz): δ 4.65 (d, 2H, J=5.37 Hz, —HNC$\underline{H}_2$-Pyr), 7.34, 8.43, 8.57 (3×m, 4H, Pyr), 8.10 (s, 1H, —N=C$\underline{H}$—NH—), 8.83 (bs, 1H, —$\underline{H}$NCH$_2$-Pyr), 13.07 (bs, 1H, —N=CH—N$\underline{H}$—). FABMS m/z (relative intensity): 245 ([M+H]$^+$, 40), 176 (27), 154 (100), 136 (74). Accurate Mass (M+H): Actual: 245.0951, Measured: 245.0942. Microanalysis (Expected: Measured) C$_{11}$H$_9$N$_6$F.0.2H$_2$O: C, 53.31; 54.03; H, 3.82; 3.83; N, 33.91; 32.74.

(2-Fluoro-9-isopropyl-9H-purin-6-yl)-pyridin-3-ylmethyl-amine

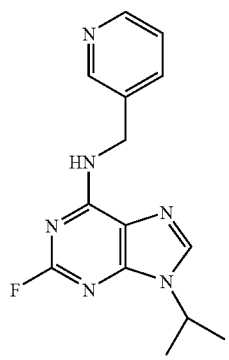 [SMILES: CC(C)n1cnc2c(NCc3cccnc3)nc(F)nc21]

To a stirred solution of (2-fluoro-9H-purin-6-yl)-pyridin-3-ylmethyl-amine (1.00 g, 1 eq, 4.10 mmol) in DMA (12 mL) under an argon atmosphere, at RT, was added K$_2$CO$_3$ (powdered, anhydrous, 2.75 g, 4.85 eq, 19.90 mmol) followed 2-bromopropane (3.75 mL, 9.75 eq, 39.93 mmol). The reaction mixture was stirred at RT for 48 h, when TLC (CHCl$_3$:MeOH; 90:10) indicated that the reaction had gone to completion. The solvent was evaporated in vacuo and the residue partitioned between water (200 mL) and EtOAc (100 mL), the aqueous phase was separated and extracted with more EtOAc (2×50 mL). The bulked organic phase was washed with brine (50 mL), dried (MgSO$_4$) and evaporated in vacuo, and the residue was purified by gradient column chromatography on silica gel, eluted with CHCl$_3$:MeOH (100:0→95:5), to afford the title compound as a white solid. Yield: 0.73 g (62%). Mp 131-133° C. $^1$H-NMR (d$_6$-DMSO, 250 MHz): δ 1.49 (2×s, 6H, —CH(C$\underline{H}_3$)$_2$), 4.63 (m, 3H, —C$\underline{H}$(CH$_3$)$_2$ & —HNC$\underline{H}_2$-Pyr), 7.34, 7.24, 8.44, 8.58 (4×m, 4H, Pyr), 8.26 (s, 1H, —N=C$\underline{H}$—N—), 8.95 (bs, 1H, —$\underline{H}$N CH$_2$-Pyr). FABMS m/z (relative intensity): 287 ([M+H]$^+$, 100), 245 (8), 154 (23), 136 (18). Accurate Mass (M+H): Actual: 287.1420, Measured: 287.1412. Microanalysis (Expected: Measured) C$_{14}$H$_{15}$N$_6$F: C, 58.73; 58.57; H, 5.28; 5.21; N, 29.35; 29.27.

(2S3R)-3-{9-Isopropyl-6-[(pyridin-3-ylmethyl)-amino]-9H-purin-2-ylamino}-pentan-2-ol

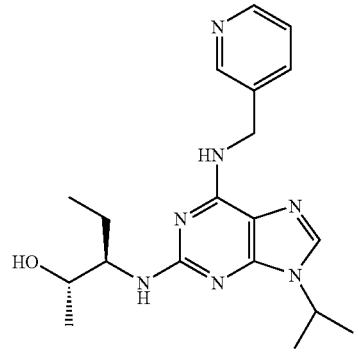

To a stirred solution of (2-fluoro-9-isopropyl-9H-purin-6-yl)-pyridin-3-ylmethyl-amine (30 mg, 1 eq, 0.10 mmol) in n-BuOH/DMSO (2.5 mL, 4:1) at room temperature under an argon atmosphere was added DIEA (0.2 mL, 10.96 eq, 1.14 mmol) followed by (2S,3R)-3-amino-pentan-2-ol (60 mg, 5.5 eq, 0.58 mmol). The reaction mixture was placed in a preheated oil bath at 160° C. and stirred at this temperature for 72 h. The reaction mixture was allowed to cool to room temperature and the solvent was evaporated in vacuo. The residue was partitioned between EtOAc (50 mL) and water (50 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$:MeOH (100:0→98:2), to afford the title compound as a white solid. Yield: 22 mg (57%). (80% de 3R,2S: 20% de 3R,2R). $^1$H-NMR (d-CDCl$_3$, 250 MHz): δ 0.90, 1.05 (2×t, 3H, J=6.95 & 7.42 Hz, —NHCH (CH$_2$C$\underline{H}_3$)CH(CH$_3$)OH), 1.17 & 1.25 (2×d, 3H, J=6.32 & 6.16 Hz, —NHCH (CH$_2$CH$_3$)CH(C$\underline{H}_3$)OH) 1.57 (d, 6H, J=6.79 Hz, —CH(C$\underline{H}_3$)$_2$), 1.77-2.09 (m, 2H, —NHCH(C$\underline{H}_2$ CH$_3$)CH (CH$_3$)OH), 3.91-4.03 (m, 2H, —NHC$\underline{H}$(CH$_2$CH$_3$) C$\underline{H}$(CH$_3$)OH), 4.58-4.69 (m, 1H, —C$\underline{H}$(CH$_3$)$_2$), 4.83-5.00 (m, 3H, —HNC$\underline{H}_2$-Pyr & OH), 6.16 (m, 1H, —N$\underline{H}$ CH(CH$_2$CH$_3$)CH(CH$_3$)OH), 7.24-7.33 (m, 3H, 2×Pyr-H & —N=C$\underline{H}$—N—), 7.55 (m, 1H, Pyr-H), 7.74 (d, 1H, J=7.42 Hz, Pyr-H), 8.67 (m, 1H, $\underline{H}$NCH$_2$-Pyr). FABMS m/z (relative intensity): 370 ([M+H]$^+$, 100), 324 (35), 289 (37), 243 (65), 199 (85). Accurate Mass (M+H): Actual: 370.2355, Measured: 370.2347.

(2R3S)-3-{9-Isopropyl-6-[(pyridin-3-ylmethyl)-amino]-9H-purin-2-ylamino}-pentan-2-ol

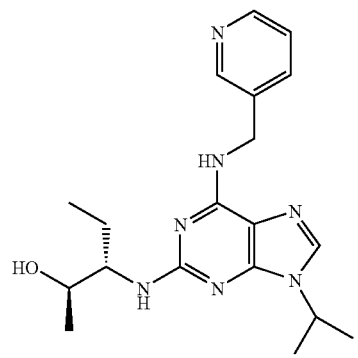 [SMILES: CC[C@H](Nc1nc(NCc2cccnc2)c2ncn(C(C)C)c2n1)[C@@H](C)O]

To a stirred solution of (2-fluoro-9-isopropyl-9H-purin-6-yl)-pyridin-3-ylmethyl-amine (30 mg, 1 eq, 0.10 mmol) in n-BuOH/DMSO (2.5 mL, 4:1) at room temperature under an argon atmosphere was added DIEA (0.2 mL, 10.96 eq, 1.14 mmol) followed by (2R,3S)-3-amino-pentan-2-ol (60 mg, 5.5 eq, 0.58 mmol). The reaction mixture was placed in a preheated oil bath at 160° C. and stirred at this temperature for 72 h. The reaction mixture was allowed to cool to room temperature and the solvent was evaporated in vacuo. The residue was partitioned between EtOAc (50 mL) and water (50 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$:MeOH (100:0→98:2), to afford the title compound as a white solid. Yield: 25 mg (65%). (80% de 3S,2R: 20% de 3S,2S). $^1$H-NMR (d-CDCl$_3$, 250 MHz): δ 0.90 & 1.05 (2×t, 3H, J=6.48 & 7.42 Hz, —NHCH(CH$_2$CH$_3$)CH(CH$_3$)OH), 1.16 & 1.24 (2×d, 3H, J=6.31 & 6.16 Hz, —NHCH(CH$_2$CH$_3$)CH(CH$_3$)OH) 1.57 (d, 6H, J=6.79 Hz, —CH(CH$_3$)$_2$), 1.77-2.09 (m, 2H, —NHCH(CH$_2$ CH$_3$)CH (CH$_3$)OH), 3.91-4.04 (m, 2H, —NHCH(CH$_2$CH$_3$) CH(CH$_3$)OH), 4.58-4.69 (m, 1H, —CH(CH$_3$)$_2$), 4.83 (m, 3H, —HNCH$_2$-Pyr & OH), 6.11-6.23 (m, 1H, —NH CH(CH$_2$CH$_3$)CH(CH$_3$)OH), 7.24-7.32 (m, 3H, 2×Pyr-H+—N=CH—N—), 7.53-7.57 (m, 1H, Pyr-H), 7.74 (d, 1H, J=7.58 Hz, Pyr-H), 8.67 (m, 1H, HNCH$_2$-Pyr). FABMS m/z (relative intensity): 370 ([M+H]$^+$, 100), 324 (40), 289 (15), 243 (10), 233 (13), 199 (10). Accurate Mass (M+H): Actual: 370.2355, Measured: 370.2347.

(3RS,4R)-4-{9-Isopropyl-6-[(pyridin-3-ylmethyl)-amino]-9H-purin-2-ylamino}-hexan-3-ol

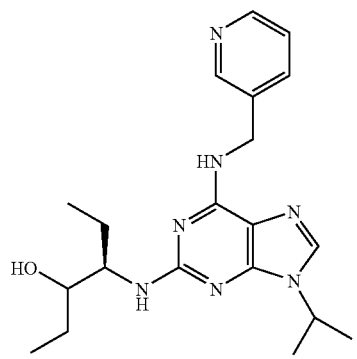 [SMILES: CCC(O)[C@@H](CC)Nc1nc(NCc2cccnc2)c2ncn(C(C)C)c2n1]

To a stirred solution of (2-fluoro-9-isopropyl-9H-purin-6-yl)-pyridin-3-ylmethyl-amine (20 mg, 1 eq, 0.07 mmol) in n-BuOH/DMSO (3.75 mL, 4:1) at room temperature under an argon atmosphere was added DIEA (0.18 mL, 15 eq, 1.03 mmol) followed by (3RS,4R)-4-amino-hexan-3-ol (110 mg, 13 eq, 0.94 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$:MeOH (100:0→98:2), to afford the title compound as a white solid. Yield: 23 mg (75%). (57% de 4R,3S: 43% de 4R,3R). $^1$H-NMR (d-CDCl$_3$, 250 MHz): δ 0.87-1.07 (m, 6H, —NHCH(CH$_2$CH$_3$)CH(CH$_2$CH$_3$)OH), 1.56 (d, 6H, J=6.63 Hz, & —CH(CH$_3$)$_2$), 1.43-1.63 (m, 4H, —NHCH(CH$_2$CH$_3$)CH(CH$_2$CH$_3$)OH), 3.44 (d, 1H, J=6.31 Hz, OH), 3.58-3.71 (m, 1H, —NHCH(CH$_2$CH$_3$) CH(CH$_2$CH$_3$)OH), 3.89-4.01 (m, 1H, —NHCH(CH$_2$CH$_3$) CH(CH$_2$CH$_3$)OH), 4.56-4.70 (m, 1H, —CH(CH$_3$)$_2$), 4.76-4.95 (m, 2H, —HNCH$_2$-Pyr), 5.20-5.29 & 6.17-6.34 (m, 1H, —NHCH(CH$_2$CH$_3$)CH(CH$_2$CH$_3$)OH), 7.19-7.38 (m, 3H, 2×Pyr-H & —N=CH—N—), 7.48-7.60 (m, 1H, Pyr-H), 7.72 (d, 1H, J=7.74 Hz, Pyr-H), 8.67 (m, 1H, HNCH$_2$-Pyr). FABMS m/z (relative intensity): 384 ([M+H]$^+$, 100), 324 (50), 297 (30). Accurate Mass (M+H): Actual: 384.2512, Measured: 384.2500.

(3RS,4S)-4-{9-Isopropyl-6-[(pyridin-3-ylmethyl)-amino]-9H-purin-2-ylamino}-hexan-3-ol

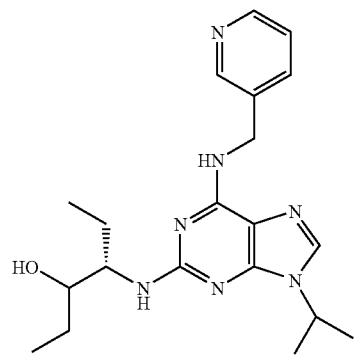

To a stirred solution of (2-fluoro-9-isopropyl-9H-purin-6-yl)-pyridin-3-ylmethyl-amine (20 mg, 1 eq, 0.07 mmol) in n-BuOH/DMSO (3.75 mL, 4:1) at room temperature under an argon atmosphere was added DIEA (0.18 mL, 15 eq, 1.03 mmol) followed by (3RS,4S)-4-amino-hexan-3-ol (110 mg, 13 eq, 0.94 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$:MeOH (100:0→98:2), to afford the title compound as a white solid. Yield: 15.5 mg (58%). (57% de 4S,3R: 43% de 4S,3S). $^1$H-NMR (d-CDCl$_3$, 250 MHz): δ 0.84-1.09 (m, 6H, —NHCH (CH$_2$CH$_3$)CH(CH$_2$CH$_3$)OH), 1.57 (d, 6H, J=6.48 Hz, & —CH(CH$_3$)$_2$), 1.42-1.64 (m, 4H, —NHCH(CH$_2$CH$_3$) CH(CH$_2$CH$_3$)OH), 3.45 (d, 1H, J=6.31 Hz, OH), 3.55-3.71 (m, 1H, —NHCH(CH$_2$CH$_3$)CH(CH$_2$CH$_3$)OH), 3.88-4.03 (m, 1H, —NHCH(CH$_2$CH$_3$)CH(CH$_2$CH$_3$)OH), 4.56-4.74 (m, 1H, —CH(CH$_3$)$_2$), 4.78-4.99 (m, 2H, —HNCH$_2$-Pyr), 5.20-5.29 & 6.20-6.39 (m, 1H, —NHCH (CH$_2$CH$_3$)CH (CH$_2$CH$_3$)OH), 7.20-7.36 (m, 3H, 2×Pyr-H+—N=CH—N—), 7.49-7.60 (m, 1H, Pyr-H), 7.72 (d, 1H, J=7.82 Hz, Pyr-H), 8.71 (m, 1H, HNCH$_2$-Pyr). FABMS m/z (relative intensity): 384 ([M+H]$^+$, 100), 324 (35), 297 (15). Accurate Mass (M+H): Actual: 384.2512, Measured: 384.2500.

(3RS,4R)-4-{9-Isopropyl-6-[(pyridin-3-ylmethyl)-amino]-9H-purin-2-ylamino}-2-methyl-hexan-3-ol

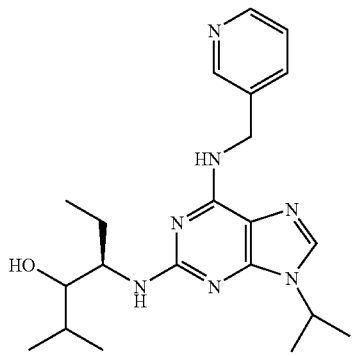

To a stirred solution of (2-fluoro-9-isopropyl-9H-purin-6-yl)-pyridin-3-ylmethyl-amine (30 mg, 1 eq, 0.10 mmol) in n-BuOH/DMSO (2.5 mL, 4:1) at room temperature under an argon atmosphere was added DIEA (0.10 mL, 5.5 eq, 0.57 mmol) followed by (3RS,4R)-4-amino-2-methyl-hexan-3-ol (42 mg, 3.0 eq, 0.32 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$: MeOH (100:0→98:2), to afford the title compound as a white solid. Yield: 6.3 mg (15%). 50% de 4R,3S: 50% de 4R,3R). $^1$H-NMR (d-CDCl$_3$, 250 MHz): δ 0.93-1.04 (m, 9H, —NHCH(CH$_2$CH$_3$)CH(CH(CH$_3$)$_2$)OH), 1.57 (d, 6H, J=6.95 Hz, —CH(CH$_3$)$_2$), 1.65-1.89 (m, 4H, —NHCH(CH$_2$CH$_3$)CH(CH(CH$_3$)$_2$)OH), 3.22-3.32 (m, 1H, —NHCH(CH$_2$CH$_3$)CH(CH(CH$_3$)$_2$)OH), 3.82-3.97 (m, 1H, —NHCH(CH$_2$CH$_3$)CH(CH(CH$_3$)$_2$)OH), 4.54-4.70 (m, 1H, —CH(CH$_3$)$_2$), 4.78-4.88 (m, 2H, —HNCH$_2$-Pyr), 5.03-5.14 & 6.08-6.20 (m, 1H, —NHCH(CH$_2$CH$_3$)CH(CH$_2$CH$_3$)OH), 7.22-7.36 (m, 3H, 2×Pyr-H & —N=CH—N—), 7.49-7.58 (m, 1H, Pyr-H), 7.71 (d, 1H, J=7.90 Hz, Pyr-H), 8.47-8.73 (m, 1H, HNCH$_2$-Pyr). FABMS m/z (relative intensity): 398 ([M+H]$^+$, 100), 324 (50). Accurate Mass (M+H): Actual: 398.2668, Measured: 398.2654.

(3RS,4S)-4-{9-Isopropyl-6-[(pyridin-3-ylmethyl)-amino]-9H-purin-2-ylamino}-2-methyl-hexan-3-ol

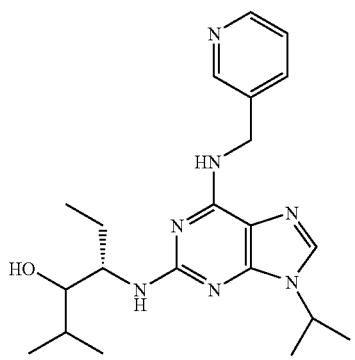 [SMILES: CCC(O)[C@H](CC)Nc1nc(NCc2cccnc2)c2ncn(C(C)C)c2n1]

To a stirred solution of (2-fluoro-9-isopropyl-9H-purin-6-yl)-pyridin-3-ylmethyl-amine (30 mg, 1 eq, 0.10 mmol) in n-BuOH/DMSO (2.5 mL, 4:1) at room temperature under an argon atmosphere was added DIEA (0.20 mL, 11 eq, 1.14 mmol) followed by (3RS,4S)-4-amino-2-methyl-hexan-3-ol (28 mg, 2.0 eq, 0.21 mmol). The reaction mixture was placed in a preheated oil bath at 160° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$: MeOH (100:0→98:2), to afford the title compound as a white solid. Yield: 4.3 mg (10%). 50% de 4S,3R: 50% de 4S,3S). $^1$H-NMR (d-CDCl$_3$, 250 MHz): δ 0.91-1.05 (m, 9H, —NHCH(CH$_2$CH$_3$)CH(CH(CH$_3$)$_2$)OH), 1.57 (d, 6H, J=6.95 Hz, —CH(CH$_3$)$_2$), 1.60-1.95 (m, 4H, —NHCH(CH$_2$CH$_3$)CH(CH(CH$_3$)$_2$)OH), 3.23-3.33 (m, 1H, —NHCH(CH$_2$CH$_3$)CH(CH(CH$_3$)$_2$)OH), 3.84-4.04 (m, 1H, —NHCH(CH$_2$CH$_3$)CH(CH(CH$_3$)$_2$)OH), 4.56-4.70 (m, 1H, —CH(CH$_3$)$_2$), 4.77-4.95 (m, 2H, —HNCH$_2$-Pyr), 5.26-5.43+6.27-6.50 (m, 1H, —NHCH(CH$_2$CH$_3$)CH(CH$_2$CH$_3$)OH), 7.23-7.37 (m, 3H, 2×Pyr-H & —N=CH—N—), 7.51-7.63 (m, 1H, Pyr-H), 7.73 (d, 1H, J=7.74 Hz, Pyr-H), 8.48-8.76 (m, 1H, HNCH$_2$-Pyr). FABMS m/z (relative intensity): 398 ([M+H]$^+$, 100), 324 (60). Accurate Mass (M+H): Actual: 398.2668, Measured: 398.2654.

(3RS,4R)-4-{9-Isopropyl-6-[(pyridin-3-ylmethyl)-amino]-9H-purin-2-ylamino}-2,2-dimethyl-hexan-3-ol

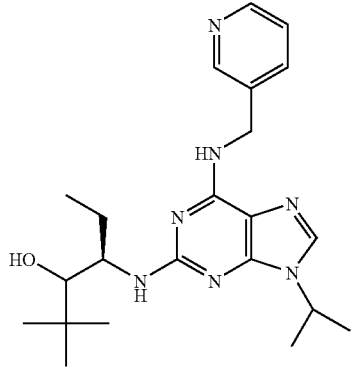

To a stirred solution of (2-fluoro-9-isopropyl-9H-purin-6-yl)-pyridin-3-ylmethyl-amine (30 mg, 1 eq, 0.10 mmol) in n-BuOH/DMSO (5 mL, 4:1) at room temperature under an argon atmosphere was added DIEA (0.10 mL, 5.5 eq, 0.57 mmol) followed by (3RS,4R)-4-amino-2,2-dimethyl-hexan-3-ol (52 mg, 3.41 eq, 0.36 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$:MeOH (100:0→98:2), to afford the title compound as a white solid. Yield: 7.3 mg (17%). (55% de 4R,3S: 45% de 4R,3R). $^1$H-NMR (d-CDCl$_3$, 250 MHz): δ 0.99-1.03 (m, 12H, —NHCH(CH$_2$CH$_3$)CH(C(CH$_3$)$_3$)OH), 1.56 & 1.58 (2×d, 6H, J=6.63 & 6.79 Hz, —CH(CH$_3$)$_2$), 1.69-1.91 (m, 2H, —NHCH(CH₂CH₃)CH(C(CH₃)₃)OH), 3.55 (d, 1H, J=1.74 Hz, —NHCH(CH₂CH₃)CH(C(CH₃)₃)OH), 3.76-3.87 (m, 1H, —NHCH(CH₂CH₃)CH(C (CH₃)₃)OH), 4.57-4.70 (m, 1H, —CH(CH₃)₂), 4.80-4.89 (m, 2H, —HNCH₂-Pyr), 5.22-5.35 & 6.07-6.23 (m, 1H, —NHCH(CH₂CH₃)CH(C(CH₃)₃)OH), 7.24-7.36 (m, 3H, 2×Pyr-H & —N═CH—N—), 7.55 (s, 1H, Pyr-H), 7.74 (d, 1H, J=7.58 Hz, Pyr-H), 8.50-8.74 (m, 1H, HNCH₂-Pyr). FABMS m/z (relative intensity): 412 ([M+H]⁺, 100), 324 (80). Accurate Mass (M+H): Actual: 412.2825, Measured: 412.2835.

(3RS,4S)-4-{9-Isopropyl-6-[(pyridin-3-ylmethyl)-amino]-9H-purin-2-ylamino}-2,2-dimethyl-hexan-3-ol

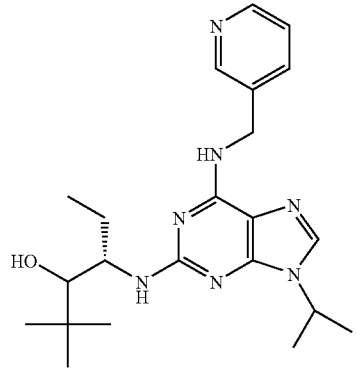 [SMILES: CC[C@H](Nc1nc(NCc2cccnc2)c2ncn(C(C)C)c2n1)C(O)C(C)(C)C]

To a stirred solution of (3RS,4R)-4-{9-Isopropyl-6-[(pyridin-3-ylmethyl)-amino]-9H-purin-2-ylamino}-2,2-dimethyl-hexan-3-ol (30 mg, 1 eq, 0.10 mmol) in n-BuOH/DMSO (5 mL, 4:1) at room temperature under an argon atmosphere was added DIEA (0.10 mL, 5.5 eq, 0.57 mmol) followed by (3RS,4S)-4-amino-2,2-dimethyl-hexan-3-ol (43 mg, 2.81 eq, 0.29 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO₄) and evaporated in vacuo. The residue was purified by gradient column chromatography on silica gel eluted with CHCl₃:MeOH (100:0→98:2), to afford the title compound as a white solid. Yield: 5.4 mg (13%). (53% de 4S,3R: 47% de 4S,3S). ¹H-NMR (d-CDCl₃, 250 MHz): δ 0.99-1.03 (m, 12H, —NHCH(CH₂CH₃)CH(C(CH₃)₃)OH), 1.57 & 1.59 (2×d, 6H, J=6.79 & 6.79 Hz, —CH(CH₃)₂), 1.70-1.93 (m, 2H, —NHCH(CH₂CH₃)CH(C(CH₃)₃)OH), 3.55 (d, 1H, J=2.05 Hz, —NHCH(CH₂CH₃)CH(C(CH₃)₃)OH), 3.77-3.90 (m, 1H, —NHCH(CH₂CH₃)CH(C(CH₃)₃)OH), 4.58-4.70 (m, 1H, —CH(CH₃)₂), 4.82-4.94 (m, 2H, —HNCH₂-Pyr), 5.31-5.45 & 6.12-6.34 (m, 1H, —NHCH(CH₂CH₃)CH (C(CH₃)₃)OH), 7.26-7.40 (m, 3H, 2×Pyr-H & —N═CH—N—), 7.55 (s, 1H, Pyr-H), 7.75 (d, 1H, J=7.42 Hz, Pyr-H), 8.46-8.81 (m, 1H, HNCH₂-Pyr). FABMS m/z (relative intensity): 412 ([M+H]⁺, 100), 324 (70). Accurate Mass (M+H): Actual: 412.2825, Measured: 412.2835.

(3R)-3-{9-Isopropyl-6-[(pyridin-3-ylmethyl)-amino]-9H-purin-2-ylamino}-2-methyl-pentan-2-ol

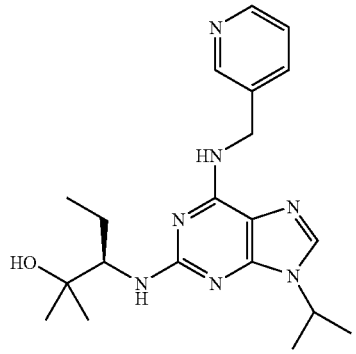

To a stirred solution of (2-fluoro-9-isopropyl-9H-purin-6-yl)-pyridin-3-ylmethyl-amine (20 mg, 1 eq, 0.07 mmol) in n-BuOH/DMSO (1.25 mL, 4:1) at room temperature under an argon atmosphere was added DIEA (0.25 mL, 20.5 eq, 1.44 mmol) followed by (3R)-3-amino-2-methyl-pentan-2-ol (22 mg, 2.7 eq, 0.19 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO₄) and evaporated in vacuo. The residue was purified by gradient column chromatography on silica gel eluted with CHCl₃:MeOH (100:0→98:2), to afford the title compound as a white solid. Yield: 3.7 mg (14%). ¹H-NMR (d-CDCl₃, 250 MHz): δ 1.00 (t, 3H, J=7.27 Hz, —NHCH(CH₂CH₃)C(CH₃)₂OH), 1.21 & 1.31 (2×s, 6H, —NHCH(CH₂CH₃)C(CH₃)₂OH), 1.57 (d, 6H, J=6.63 Hz, —CH(CH₃)₂), 1.69-1.89 (m, 2H, —NHCH(CH₂CH₃)C(CH₃)₂OH), 3.66-3.83 (m, 1H, —NHCH(CH₂CH₃)C(CH₃)₂OH), 4.59-4.73 (m, 1H, —CH(CH₃)₂), 4.77-5.00 (m, 2H, —HNCH₂-Pyr), 7.26-7.46 (m, 3H, 2×Pyr-H & —N═CH—N—), 7.49-7.69 (m, 1H, Pyr-H), 7.78 (d, 1H, J=7.10 Hz, Pyr-H). FABMS m/z (relative intensity): 384 ([M+H]⁺, 65), 366 (23), 324 (100), 217 (35), 192 (55). Accurate Mass (M+H): Actual: 384.2512, Measured: 384.2494.

(3S)-3-{9-Isopropyl-6-[(pyridin-2-ylmethyl)-amino]-9H-purin-3-ylamino}-2-methyl-pentan-2-ol

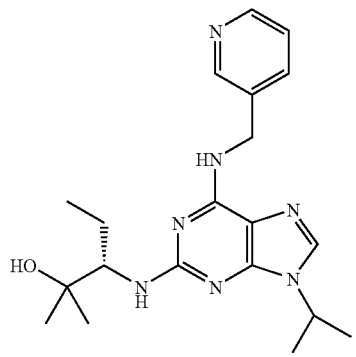

To a stirred solution of (2-fluoro-9-isopropyl-9H-purin-6-yl)-pyridin-3-ylmethyl-amine (30 mg, 1 eq, 0.10 mmol) in n-BuOH/DMSO (1.25 mL, 4:1) at room temperature under an argon atmosphere was added DIEA (0.25 mL, 14.4 eq, 1.44 mmol) followed by (3S)-3-amino-2-methyl-pentan-2-ol (40 mg, 3.2 eq, 34 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×25 mL), and the combined organic phase was washed with brine (50 mL), dried (MgSO$_4$) and evaporated in vacuo. The residue was purified by gradient column chromatography on silica gel eluted with CHCl$_3$:MeOH (100:0→98:2), to afford the title compound as a white solid. Yield: 6.5 mg (16%). $^1$H-NMR (d-CDCl$_3$, 250 MHz): δ 1.00 (t, 3H, J=7.42 Hz, —NHCH(CH$_2$CH$_3$)C(CH$_3$)$_2$OH), 1.22 & 1.31 (2×s, 6H, —NHCH(CH$_2$CH$_3$)C(CH$_3$)$_2$OH), 1.57 (d, 6H, J=6.79 Hz, —CH(CH$_3$)$_2$), 1.70-1.90 (m, 2H, —NHCH(CH$_2$ CH$_3$)C(CH$_3$)$_2$OH), 3.66-3.81 (m, 1H, —NHCH(CH$_2$CH$_3$)C(CH$_3$)$_2$OH), 4.56-4.73 (m, 1H, —CH(CH$_3$)$_2$), 4.78-5.01 (m, 2H, —HNCH$_2$-Pyr), 7.20-7.45 (m, 3H, 2×Pyr-H & —N=CH—N—), 7.48-7.69 (m, 1H, Pyr-H), 7.77 (d, 1H, J=7.74 Hz, Pyr-H). FABMS m/z (relative intensity): 384 ([M+H]$^+$, 100), 366 (30), 324 (85), 286 (40), 242 (65), 192 (63), 176 (70). Accurate Mass (M+H): Actual: 384.2512, Measured: 384.2494.

For the large-scale preparation of the individual enantiomers of 3-{9-isopropyl-6-[(pyridin-3-ylmethyl)-amino]-9H-purin-2-ylamino}-2-methyl-pentan-2-ol 24 (Scheme 3 below), a different procedure was adopted. Dichloropurine 14 was aminated at C-6 with pyridylmethylamine 15 to afford intermediate 16, which was then alkylated at N-9 with 2-bromopropane 17. The resulting chloropurine 18 was aminated at C-2 with the appropriate enantiomer of 3-amino-2-methyl-pentan-2-ol 23.

Scheme 3

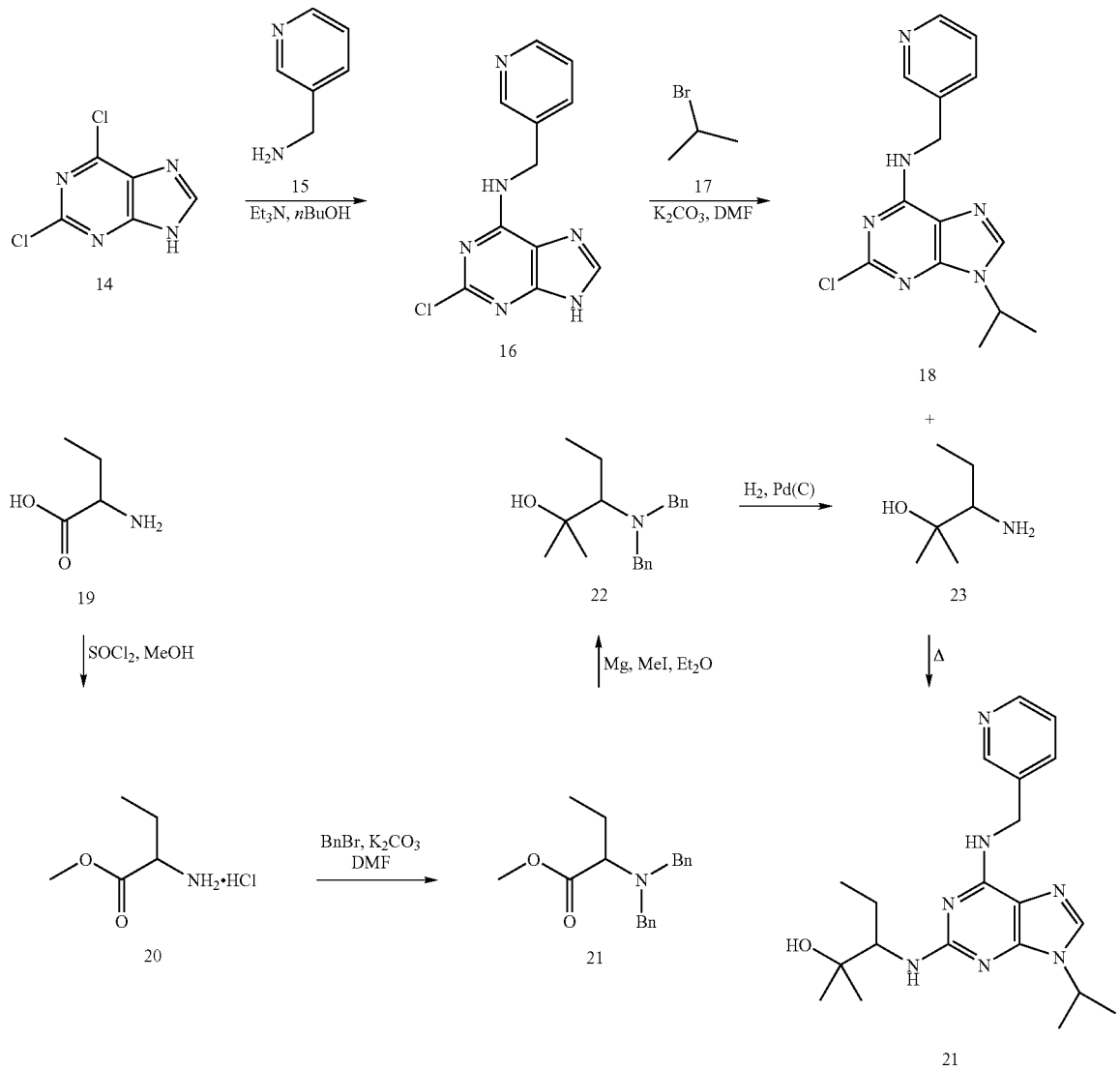

It has previously been demonstrated that optically pure R-3-amino-2-methyl-pentan-2-ol 23 can be obtained directly by conversion of R-2-amino-butyric acid 19 to the methyl ester 20, followed by double Grignard methylation (Guenther, B. R.; Kirmse, W. Liebigs Ann. Chem., 1980, 518). This method was not suitable for scale-up work in terms of yield and product purity. Protection of the amino group as the dibenzyl derivative (21, Bn=benzyl) was therefore adopted. Methylation of amino ester 21 provided alcohol 22 in high yield and purity. The benzyl groups were then removed hydrogenolytically to afford the pure enantiomers of 3-amino-2-methyl-pentan-2-ol 23.

(2-Chloro-9H-purin-6-yl)-pyridin-3-ylmethyl-amine

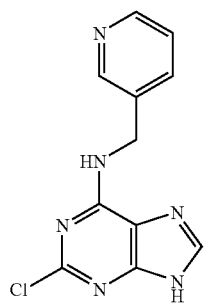 [SMILES: Clc1nc(NCc2cccnc2)c2nc[nH]c2n1]

2,6-Dichloro-9H-purine (157.2 g, 0.83 mol), butan-1-ol (1.2 L), and Et₃N (290 mL, 2.08 mol) were stirred and heated to 50° C. 3-C-Pyridin-3-yl-methylamine (94 mL, 0.76 mol) was added and the reaction heated to 120° C. for 1 h. Heating was ceased and the flask allowed to cool to ambient temperature then to 0° C. using an ice-water bath. The peach-coloured precipitate was collected by filtration, washed with H₂O (1 L), hexane (2×0.5 L) and dried to leave a peach-coloured solid. A second crop was obtained by evaporation of the combined filtrate and washings, trituration with H₂O (100 mL) and CHCl₃ (100 ml), filtration, washing with hexane, and drying. The crops were combined to provide the title compound (196 g, 91%). ¹H-NMR (DMSO-d₆): δ 4.67-4.69 (2H, d, —C$\underline{H}_2$—NH—), 5.20 (1H, br. s, N$\underline{H}$), 7.34-7.39 (dd, ArH), 7.76-7.79 (1H, d, ArH), 8.17 (1H, s, ArH—N=C$\underline{H}$—N—), 8.46-8.48 (1H, d, ArH), 8.61 (1H, s, ArH), 8.80 (1H, br. s, N$\underline{H}$).

(2-Chloro-9-isopropyl-9H-purin-6-yl)-pyridin-3-ylmethyl-amine

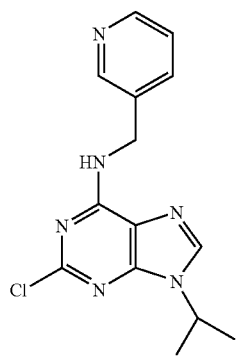 [SMILES: CC(C)n1cnc2c(NCc3cccnc3)nc(Cl)nc21]

(2-Chloro-9H-purin-6-yl)-pyridin-3-ylmethyl-amine (110.3 g, 0.37 mol) was dissolved in dry DMF (1.5 L) and warmed to 70° C. with stirring. K₂CO₃ (230 g, 1.67 mol) and 2-bromopropane (300 mL, 3.20 mol) were added and the reaction was stirred at 70° C. overnight. The reaction mixture was allowed to cool to room temperature and K₂CO₃ was removed by filtration and washing with EtOAc. The combined filtrate and washings were concentrated on a rotary evaporator and then under high vacuum to remove most of the DMF. The resulting residue was stirred vigorously in H₂O (1 L) and CH₂Cl₂ (1 L) until dissolution was complete. The aqueous layer was extracted with more CH₂Cl₂ (2×200 mL), the organic extracts were combined, dried over MgSO₄, and evaporated to afford the title compound (87.2 g, 78%) as a beige powder. ¹H-NMR (DMSO-d₆): δ 1.50-1.53 (6H, d, —CH(C$\underline{H}_3$)₂), 4.67-4.72 (3H, m, —C$\underline{H}_2$—NH— & —C$\underline{H}$(CH₃)₂), 5.20 (1H, br. s, N$\underline{H}$), 7.34-7.39 (dd, ArH), 7.76-7.79 (1H, d, ArH), 8.33 (1H, s, ArH, —N=C$\underline{H}$—N—), 8.46-8.48 (1H, d, ArH), 8.61 (1H, s, ArH), 8.92 (1H, br. s, N$\underline{H}$).

R-2-Amino-butyric acid methyl ester hydrochloride

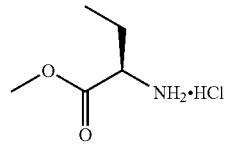

(D)-(−)-2-Aminobutyric acid (50.0 g, 0.48 mol) was suspended in MeOH (270 mL) and cooled to −10° C. (ice-salt bath) with stirring, under N₂. SOCl₂ (64 mL, 0.864 mol) was added dropwise, over 90 min. The flask was fitted with a reflux condenser and heated to 70° C. for 1 h then cooled and evaporated (co-evaporating with MeOH). The residue was broken up and dried under high vacuum to afford the title compound as a white powder (75 g, 100%). ¹H-NMR (CDCl₃): δ 0.88-0.95 (3H, t, C$\underline{H}_3$CH₂—), 1.48 (2H, br. s, NH₂), 1.50-1.80 (2H, m, CH₃C$\underline{H}_2$—), 3.35-3.40 (1H, t, C$\underline{H}$NH₂), 3.69 (3H, s, OC$\underline{H}_3$).

R-2-Dibenzylamino-butyric acid methyl ester

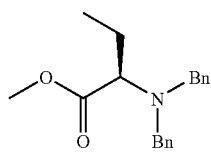 [SMILES: CC[C@H](C(=O)OC)N(Cc1ccccc1)Cc1ccccc1]

To R-2-amino-butyric acid methyl ester hydrochloride (74.5 g, 0.485 mol) in dry DMF (500 mL) under N₂ at room temperature was added K₂CO₃ (147 g, 1.065 mol), followed by dropwise addition of benzyl bromide (127 mL, 1.065 mol.). After 2 h stirring K₂CO₃ was filtered off and washed (EtOAc, 200 mL). The combined filtrate and washings were evaporated in vacuo. The oily residue was partitioned between EtOAc (1.5 L) and H₂O (1.5 L). The organic layer was separated and the aqueous layer was extracted with more EtOAc (1 L). The combined organic fractions were concentrated. The residue was purified by dry silica gel flash chromatography (3:7 CH₂Cl₂/hexane). Pure fractions were combined, concentrated in vacuo, and dried to afford the title compound (136.1 g, 94%). ¹H-NMR (CDCl₃): δ 0.90-0.96 (3H, t, CH₃CH₂—), 1.75-1.81 (2H, m, CH₃—CH₂—), 3.23-3.29 (1H, t, —CH₂—CH—), 3.50-3.57 (2H, d, —NCH₂Ph), 3.77 (3H, s, —OCH₃), 3.93-3.99 (2H, d, —NCH₂Ph), 7.22-7.41 (10H, m, ArH).

R-3-Dibenzylamino-2-methyl-pentan-2-ol

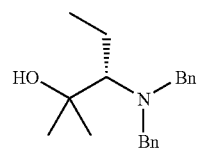 [SMILES: CC[C@H](N(Cc1ccccc1)Cc1ccccc1)C(C)(C)O]

To a dried 5-L 3-necked flask fitted with a condenser and N₂ bubbler were charged Mg turnings (53.7 g, 2.22 mol) and dry Et₂O (2 L). The mixture was stirred and cooled to 0° C. using an ice bath. MeI (138.2 mL, 2.22 mol) was then added dropwise, over 1 h. R-2-Dibenzylamino-butyric acid methyl ester in dry Et₂O (1 L) was then added slowly (over 10 min) and the reaction was allowed to warm to room temperature, becoming very thick. The reaction was left stirring for 72 h, cooled to 0° C. and quenched by slow addition of saturated aq NH₄Cl solution (350 g in 1 L). After 30 min stirring, the reaction mixture was filtered through a pad of Celite and washed with Et₂O (3×0.5 L). The ethereal layer was separated and the aqueous layer extracted with more Et₂O (1 L). The organic fractions were combined, dried over MgSO₄ and concentrated The residue was purified by silica gel flash chromatography (2% EtOAc in hexane) to afford the title compound (88.4 g, 82%) as a colourless oil. ¹H-NMR (CDCl₃): δ 1.06 (3H, s, —CCH₃), 1.15-1.26 (6H, m (3H s & 3H m, —CCH₃ & —CH₂CH₃), 1.50-1.70 (1H, m, —CHHCH₃), 1.70-1.90 (1H, m, —CHHCH₃), 2.59-2.64 (1H, dd, —CHN—), 3.61-3.67 (2H, d, —NCH₂Ph), 3.97-4.02 (2H, d, —NCH₂Ph), 4.25 (1H, br. s, —OH), 7.24-7.37 (10H, m, ArH).

R-3-Amino-2-methyl-pentan-2-ol

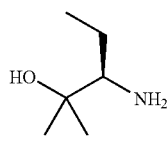

R-3-Dibenzylamino-2-methyl-pentan-2-ol (21.0 g, 70.9 mmol) and Pd(C) (2.1 g, 20% Pd by dry weight, 50% H₂O) in MeOH (100 mL) were shaken in a Parr hydrogenator at 65 psi overnight. The catalyst was removed by filtration through a pad of Celite, the filtrate concentrated and dried under high vacuum to afford the title compound as a clear yellow oil (7.585 g, 91%). ¹H-NMR (CDCl₃): δ 0.90-1.05 (6H, m (3H s & 3H m), —CCH₃ & —CH₂CH₃), 1.18 (3H, s, —CCH₃), 1.55-1.62 (2H, m, —CH₂CH₃), 1.88-2.25 (2H, br. s, —NH₂), 2.35-2.40 (1H, dd, —CHN—).

(3R)-3-{9-Isopropyl-6-[(pyridin-3-ylmethyl)-amino]-9H-purin-2-ylamino}-2-methyl-pentan-2-ol

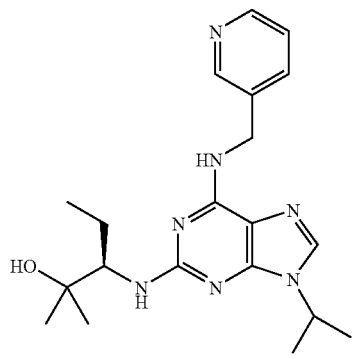

(2-Chloro-9-isopropyl-9H-purin-6-yl)-pyridin-3-ylmethyl-amine (24.4 g, 82.4 mmol), R-3-amino-2-methyl-pentan-2-ol (24.4 g, 209 mmol), and K₂CO₃ (24.4 g, 177 mmol) were heated to 150° C. for 72 h under N₂. The mixture was cooled, diluted with CH₂Cl₂, and K₂CO₃ removed by filtration. The filtrate was evaporated, then distilled (Kugelrohr) under high vacuum to remove unreacted R-3-amino-2-methyl-pentan-2-ol. The residue was subjected to two rounds of silica gel flash chromatography (first column eluted with 5 to 10% linear gradient of MeOH in CH₂Cl₂; second column eluted with 2.5% MeOH in CH₂Cl₂). The residue was dissolved in hot EtOAc (150 mL), the solution concentrated to a volume of approximately 100 mL and allowed to cool. Et₂O (10 mL) was added to induce crystallization and the solution was cooled to 0° C. The crystals were collected by filtration, washed with a little Et₂O and dried to afford pure title compound (5.70 g, 18%) as an off-white solid. The combined filtrate and washings were concentrated, the residue redissolved in the minimum volume of hot Me₂CO and allowed to cool. The solid product was filtered and redissolved in the minimum volume of hot EtOAc and allowed to cool. The solids formed were removed by filtration and the filtrate was again concentrated to dryness, redissolved in a mixture of hot Me₂CO and EtOAc, cooled, filtered and dried to afford a second crop of pure title compound (2.15 g, 5.6 mmol, 7%) as an off-white solid. M.p. 138-145° C. $[\alpha]_D^{20}$+32.54 (c 0.48, MeOH). LC-MS: 97.86% pure, m/z 384 [M+H]⁺, 406 [M+Na]⁺, C₂₀H₂₉N₇O=383.49. Microanalysis (% found (theory)): C, 62.41; (62.64); H, 7.56; (7.62); N, 25.76; (25.57). ¹H-NMR (CDCl₃): δ 0.93-0.99 (3H, t, —CH₂CH₃), 1.17 & 1.27 (6H, 2s, —C(CH₃)₂OH), 1.51-1.54 (6H, d, —NCH(CH₃)₂), 1.65-1.80 (2H, m, —CH₂CH₃), 2.15 (1H, br. s, NH or OH), 3.60-3.67 (m, 1H, —NHCH(CH₂CH₃)—), 4.57-4.62 (1H, m, —NCH(CH₃)₂), 4.77-4.80 (2H, m, —HNCH₂-Pyr), 5.15 (br. s, 1H, NH or OH), 6.14 (1H, br. s, NH or OH), 7.21-7.26 (1H, m, Pry-H), 7.48 (1H, s, —N=CH—N—), 7.68-7.71 (app. d, 1H, Pyr-H), 8.51-8.52 (app. d, 1H, Pyr-H), 8.64 (1H, app. s, Pyr-H). ¹³C-NMR (CDCl₃): consistent with structure containing 20 C atoms; 10 aliphatic C at δ 10.21, 20.88, 20.92, 21.90, 23.09, 26.64, 40.29 (weak), 44.72, 61.70 & 72.45 ppm; and 10 aromatic C at 112.96, 121.73, 132.97, 133.07, 133.65, 146.98, 147.67, 148.89 (weak), 152.97 & 158.77 ppm.

(3S)-3-{9-Isopropyl-6-[(pyridin-3-ylmethyl)-amino]-9H-purin-2-ylamino}-2-methyl-pentan-2-ol

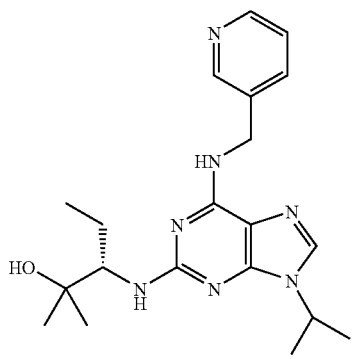 [SMILES: CC[C@H](Nc1nc(NCc2cccnc2)c2ncn(C(C)C)c2n1)C(C)(C)O]

This compound was obtained using procedures analogous to those described above for the (R) enantiomer but starting with (L)-(+)-2-aminobutyric acid. M.p. 140.5-146° C. $[\alpha]_D^{20}$ –29.00 (c 0.46, MeOH). LC-MS: 97.85% pure, m/z 384 [M+H]$^+$, $C_{20}H_{29}N_7O$=383.49. Microanalysis (% found (theory)): C, 62.51; (62.64); H, 7.61; (7.62); N, 25.70; (25.57). $^1$H-NMR: δ 0.93-0.99 (3H, t, —CH$_2$CH$_3$), 1.17 & 1.27 (6H, 2s, —C(CH$_3$)$_2$OH), 1.51-1.54 (6H, d, —NCH(CH$_3$)$_2$), 1.65-1.80 (2H, m, —CH$_2$CH$_3$), 2.15 (1H, br. s, NH or OH), 3.60-3.67 (m, 1H, —NHCH(CH$_2$CH$_3$)—), 4.57-4.62 (1H, m, —NCH(CH$_3$)$_2$), 4.77-4.80 (2H, m, —HNCH$_2$-Pyr), 5.15 (br. s, 1H, NH or OH), 6.14 (1H, br. s, NH or OH), 7.21-7.26 (1H, m, Pry-H), 7.48 (1H, s, —N=CH—N—), 7.68-7.71 (app. d, 1H, Pyr-H), 8.51-8.52 (app. d, 1H, Pyr-H), 8.64 (1H, app. s, Pyr-H). $^{13}$C-NMR (CDCl$_3$): consistent with structure containing 20 C atoms; 10 aliphatic C at δ 10.21, 20.88, 20.92, 21.90, 23.09, 26.64, 40.27 (weak), 44.71, 61.70 & 72.45 ppm; and 10 aromatic C at 112.95, 121.72, 132.96, 133.07, 133.65, 146.85, 146.98, 148.86 (weak), 152.97 & 158.77 ppm.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

TABLE 1

| | Kinase inhibition (μM) | | | | | | | | | |
| | CDK2/ cyclin E | | CDK1/ cyclin B | | CDK4/ cyclin D1 | | CDK7/ cyclin H | | PKA | ERK2 |
| Name | IC$_{50}$ | SD | IC$_{50}$ | SD | IC$_{50}$ | SD | IC$_{50}$ | SD | IC$_{50}$ | IC$_{50}$ | SD |
|---|---|---|---|---|---|---|---|---|---|---|---|
| Roscovitine | 0.10 | 0.10 | 2.7 | 2.5 | 14 | 4 | 0.49 | 0.26 | >50 | 1.2 | 1.3 |
| (2S3R)-3-{9-Isopropyl-6-[(pyridin-3-ylmethyl)-amino]-9H-purin-2-ylamino}-pentan-2-ol | 0.09 | 0.02 | 4.9 | 0.3 | 14 | 4 | 0.50 | 0.40 | >200 | 23 | 12 |
| (2R3S)-3-{9-Isopropyl-6-[(pyridin-3-ylmethyl)-amino]-9H-purin-2-ylamino}-pentan-2-ol | 0.03 | 0.01 | 2.2 | 1.2 | 6.8 | 3.2 | 1.3 | 1.0 | >200 | 20 | 6 |
| (3RS,4R)-4-{9-Isopropyl-6-[(pyridin-3-ylmethyl)-amino]-9H-purin-2-ylamino}-hexan-3-ol | 0.22 | 0.10 | 12 | 1 | 25 | 0 | 1.1 | 0.3 | >200 | 37 | 6 |
| (3RS,4S)-4-{9-Isopropyl-6-[(pyridin-3-ylmethyl)-amino]-9H-purin-2-ylamino}-hexan-3-ol | 0.11 | 0.04 | 13 | 4 | 11 | 1 | 1.5 | 0.6 | >200 | 17 | 8 |
| (3RS,4R)-4-{9-Isopropyl-6-[(pyridin-3-ylmethyl)-amino]-9H-purin-2-ylamino}-2-methyl-hexan-3-ol | 0.69 | 0.30 | 20 | 8 | 21 | 15 | 2.2 | 1.4 | 200 | 111 | 11 |
| (3RS,4S)-4-{9-Isopropyl-6-[(pyridin-3-ylmethyl)-amino]-9H-purin-2-ylamino}-2-methyl-hexan-3-ol | 1.1 | 0.6 | 22 | 12 | 31 | 9 | 3.5 | 0.4 | >200 | 67 | 6 |
| (3RS,4R)-4-{9-Isopropyl-6-[(pyridin-3-ylmethyl)-amino]-9H-purin-2-ylamino}-2,2-dimethyl-hexan-3-ol | 1.0 | 0.0 | 23 | 8 | 24 | 3 | 1.6 | 0.1 | >200 | 51 | 8 |
| (3RS,4S)-4-{9-Isopropyl-6-[(pyridin-3-ylmethyl)-amino]-9H-purin-2-ylamino}-2,2-dimethyl-hexan-3-ol | 0.39 | 0.27 | 21 | 2 | 13 | 0 | 3.5 | 0.6 | >200 | 23 | 4 |
| (3R)-3-{9-Isopropyl-6-[(pyridin-3-ylmethyl)-amino]-9H-purin-2-ylamino}-2-methyl-pentan-2-ol | 0.20 | 0.08 | 6.2 | 1.1 | 7.5 | 5 | 3.1 | 0.4 | >200 | 91 | 21 |
| (3S)-3-{9-Isopropyl-6-[(pyridin-3-ylmethyl)-amino]-9H-purin-2-ylamino}-2-methyl-pentan-2-ol | 0.07 | 0.01 | 4.4 | 1.9 | 12 | 1 | 2.5 | 1.5 | >200 | 35 | 10 |

TABLE 2

| Name | In vitro anti-proliferative activity (72-h MTT $IC_{50}$, µM) | |
|---|---|---|
| | $IC_{50}$[a] | Stand. Dev. |
| Roscovitine | 12 | 3 |
| (2S3R)-3-{9-Isopropyl-6-[(pyridin-3-ylmethyl)-amino]-9H-purin-2-ylamino}-pentan-2-ol | 1.5 | 0.4 |
| (2R3S)-3-{9-Isopropyl-6-[(pyridin-3-ylmethyl)-amino]-9H-purin-2-ylamino}-pentan-2-ol | 0.8 | 0.3 |
| (3RS,4R)-4-{9-Isopropyl-6-[(pyridin-3-ylmethyl)-amino]-9H-purin-2-ylamino}-hexan-3-ol | 10 | 1 |
| (3RS,4S)-4-{9-Isopropyl-6-[(pyridin-3-ylmethyl)-amino]-9H-purin-2-ylamino}-hexan-3-ol | 5.5 | 2.8 |
| (3RS,4R)-4-{9-Isopropyl-6-[(pyridin-3-ylmethyl)-amino]-9H-purin-2-ylamino}-2-methyl-hexan-3-ol | 28 | 10 |
| (3RS,4S)-4-{9-Isopropyl-6-[(pyridin-3-ylmethyl)-amino]-9H-purin-2-ylamino}-2-methyl-hexan-3-ol | 19 | 2 |
| (3RS,4R)-4-{9-Isopropyl-6-[(pyridin-3-ylmethyl)-amino]-9H-purin-2-ylamino}-2,2-dimethyl-hexan-3-ol | 19 | 2 |
| (3RS,4S)-4-{9-Isopropyl-6-[(pyridin-3-ylmethyl)-amino]-9H-purin-2-ylamino}-2,2-dimethyl-hexan-3-ol | 15 | 14 |
| (3R)-3-{9-Isopropyl-6-[(pyridin-3-ylmethyl)-amino]-9H-purin-2-ylamino}-2-methyl-pentan-2-ol | 5.6 | 2.1 |
| (3S)-3-{9-Isopropyl-6-[(pyridin-3-ylmethyl)-amino]-9H-purin-3-ylamino}-2-methyl-pentan-2-ol | 4.0 | 0.5 |

[a]Human tumour cell lines: A549, HT29, Saos-2

TABLE 3

| Cell line | | | 72-h MTT $IC_{50}$ (µM) | | | |
|---|---|---|---|---|---|---|
| | | | Roscovitine | (2S3R)-3-{9-Isopropyl-6-[(pyridin-3-ylmethyl)-amino]-9H-purin-2-ylamino}-pentan-2-ol | (2R3S)-3-{9-Isopropyl-6-[(pyridin-3-ylmethyl)-amino]-9H-purin-2-ylamino}-pentan-2-ol | (3S)-3-{9-Isopropyl-6-[(pyridin-3-ylmethyl)-amino]-9H-purin-3-ylamino}-2-methyl-pentan-2-ol |
| Code | Type | Source | | | | |
| A549 | Adherent | Lung carcinoma | 9.7 ± 1.1 | 2.1 ± 0.4 | 0.9 ± 0.1 | 3.6 ± 0.2 |
| HeLa | Adherent | Cervical adenocarcinoma | 16.5 ± 1.8 | 2.9 ± 0.2 | 1.4 ± 0.2 | 4.7 ± 0.5 |
| HT-29 | Adherent | Colorectal adenocarcinoma | 10.2 ± 2.7 | 2.3 ± 0.6 | 1.1 ± 0.2 | 2.3 ± 0.9 |
| MCF7 | Adherent | Mammary adenocarcinoma | 8.7 ± 0.5 | 1.6 ± 0.2 | 0.7 ± 0.1 | 2.3 ± 0.3 |
| Saos-2 | Adherent | Osteosarcoma | 15.3 ± 4.2 | 2.8 ± 0.1 | 1.2 ± 0.2 | 3.9 ± 0.8 |
| CCRF-CEM | Suspension | Acute lymphoblastic leukaemia | 16.4 ± 0.8 | n.d. | n.d. | 3.7 ± 0.3 |
| HL-60 | Suspension | Acute promyelocytic leukaemia | 13.3 ± 1.1 | n.d. | n.d. | 3.0 ± 0.2 |
| K-562 | Suspension | Chronic myelogenous leukaemia | 40.4 ± 4.4 | n.d. | n.d. | 8.4 ± 1.2 |
| | | Mean (cancer cell lines) | 16.3 ± 10.2 | 2.3 ± 0.5 | 1.1 ± 0.3 | 4.0 ± 2.0 |
| Hs27 | Normal | Foreskin fibroblast | >20 | 10.2 ± 0.6 | 5.9 ± 0.3 | 11.3 ± 0.7 |
| IMR90 | Normal | Embryo lung fibroblast | >20 | >20 | >20 | >20 |
| WI38 | Normal | Foetal lung fibroblast | >20 | 11.2 ± 1.2 | 6.1 ± 0.3 | >20 |
| | | Mean (normal cell lines) | >20 | >10 | >10 | >10 |

TABLE 4

| Name | Clog P | % Drug after 30 min. microsomal incubation | A: % Compound remaining/% roscovitine remaining | B: IC$_{50}$ CDK2 roscovitine/ IC$_{50}$ CDK2 compound | C: IC$_{50}$ cytotox. roscovitine/ IC$_{50}$ cytotox. compound | A × B | A × C |
|---|---|---|---|---|---|---|---|
| Roscovitine | 3.7 | 33 | 1.0 | 1.0 | 1.0 | 1.0 | 1.0 |
| (2S3R)-3-{9-Isopropyl-6-[(pyridin-3-ylmethyl)-amino]-9H-purin-2-ylamino}-pentan-2-ol | 2.5 | 90 | 2.7 | 1.1 | 8.0 | 3.1 | 22 |
| (2R3S)-3-{9-Isopropyl-6-[(pyridin-3-ylmethyl)-amino]-9H-purin-2-ylamino}-pentan-2-ol | 2.5 | 67 | 2.0 | 3.7 | 14 | 7.5 | 29 |
| (3RS,4R)-4-{9-Isopropyl-6-[(pyridin-3-ylmethyl)-amino]-9H-purin-2-ylamino}-hexan-3-ol | 3.0 | 70 | 2.1 | 0.5 | 1.1 | 1.0 | 2.4 |
| (3RS,4S)-4-{9-Isopropyl-6-[(pyridin-3-ylmethyl)-amino]-9H-purin-2-ylamino}-hexan-3-ol | 3.0 | 73 | 2.2 | 1.0 | 2.1 | 2.1 | 4.7 |
| (3RS,4S)-4-{9-Isopropyl-6-[(pyridin-3-ylmethyl)-amino]-9H-purin-2-ylamino}-2,2-dimethyl-hexan-3-ol | 3.8 | 50 | 1.5 | 0.3 | 0.8 | 0.4 | 1.2 |
| (3R)-3-{9-Isopropyl-6-[(pyridin-3-ylmethyl)-amino]-9H-purin-2-ylamino}-2-methyl-pentan-2-ol | 2.9 | 84 | 2.6 | 0.5 | 2.1 | 1.3 | 5.3 |
| (3S)-3-{9-Isopropyl-6-[(pyridin-3-ylmethyl)-amino]-9H-purin-3-ylamino}-2-methyl-pentan-2-ol | 2.9 | 78 | 2.4 | 1.4 | 2.9 | 3.2 | 6.9 |

The invention claimed is:

1. A compound, (2R3S)-3-{9-isopropyl-6-[(pyridin-3-yl-methyl)-amino]-9H-purin-2-ylamino}-pentan-2-ol,

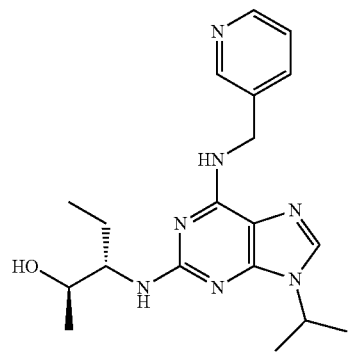 [SMILES: CC[C@H](Nc1nc(NCc2cccnc2)c2ncn(C(C)C)c2n1)[C@@H](C)O]

and pharmaceutically acceptable salts thereof.

2. A compound, (2S3R)-3-{9-isopropyl-6-[(pyridin-3-yl-methyl)-amino]-9H-purin-2-ylamino}-pentan-2-ol,

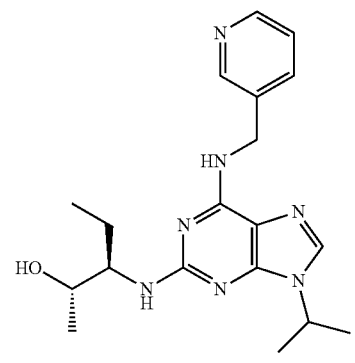 [SMILES: CC[C@@H](Nc1nc(NCc2cccnc2)c2ncn(C(C)C)c2n1)[C@H](C)O]

and pharmaceutically acceptable salts thereof.

3. A compound, (3S)-3-{9-isopropyl-6-[(pyridin-3-ylmethyl)-amino]-9H-purin-2-ylamino}-2-methyl-pentan-2-ol,

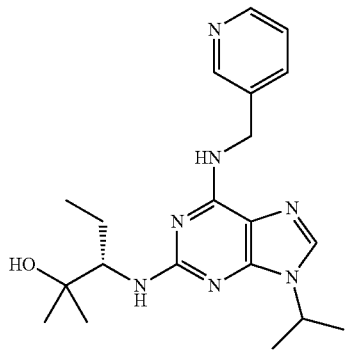 [SMILES: CC[C@H](Nc1nc(NCc2cccnc2)c2ncn(C(C)C)c2n1)C(C)(C)O]

and pharmaceutically acceptable salts thereof.

4. A compound, (3R)-3-{9-isopropyl-6-[(pyridin-3-ylmethyl)-amino]-9H-purin-2-ylamino}-2-methyl-pentan-2-ol,

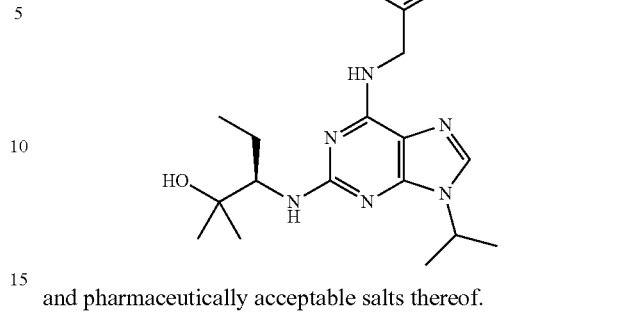

and pharmaceutically acceptable salts thereof.

5. A pharmaceutical composition comprising a compound according to any one of claim 1 or 2 admixed with a pharmaceutically acceptable diluent, excipient or carrier, or a mixture thereof.

6. A pharmaceutical composition comprising a compound according to any one of claim 3 or 4 admixed with a pharmaceutically acceptable diluent, excipient or carrier, or a mixture thereof.

* * * * *